(12) United States Patent (10) Patent No.: US 9,347,919 B2
Fukumoto et al. (45) Date of Patent: May 24, 2016

(54) GAS-LIQUID CONTACT EXTRACTION METHOD AND APPARATUS

(71) Applicants: Shimadzu Corporation, Kyoto (JP); GL Sciences Incorporation, Tokyo (JP)

(72) Inventors: Shinji Fukumoto, Kyoto (JP); Hiroshi Yamauchi, Kyoto (JP); Akira Aono, Kyoto (JP); Manabu Shimomura, Kyoto (JP); Yoshiyuki Takei, Saitama (JP); Tadashi Mimura, Saitama (JP); Akira Suzuki, Saitama (JP); Masahiro Furuno, Saitama (JP)

(73) Assignees: Shimadzu Corporation (JP); GL Sciences Incorporated (JP)

( * ) Notice: Subject to any disclaimer, the term of this patent is extended or adjusted under 35 U.S.C. 154(b) by 30 days.

(21) Appl. No.: 14/358,744

(22) PCT Filed: Nov. 16, 2012

(86) PCT No.: PCT/JP2012/079865
§ 371 (c)(1),
(2) Date: May 16, 2014

(87) PCT Pub. No.: WO2013/073693
PCT Pub. Date: May 23, 2013

(65) Prior Publication Data
US 2014/0326045 A1   Nov. 6, 2014

(30) Foreign Application Priority Data
Nov. 17, 2011   (JP) .................................. 2011-252011

(51) Int. Cl.
*G01N 30/06* (2006.01)
*G01N 1/14* (2006.01)
*G01N 1/24* (2006.01)
*B01D 3/34* (2006.01)
(Continued)

(52) U.S. Cl.
CPC ................. *G01N 30/06* (2013.01); *B01D 3/346* (2013.01); *G01N 1/14* (2013.01); *G01N 1/24* (2013.01);
(Continued)

(58) Field of Classification Search
CPC ............ G01N 1/40; G01N 2001/4033; G01N 2001/4066; G01N 30/06; G01N 2030/065; B01D 3/343; B01D 3/346
See application file for complete search history.

(56) References Cited

U.S. PATENT DOCUMENTS 5,792,663 A     8/1998 Fry et al.

FOREIGN PATENT DOCUMENTS

JP     10-010050 A     1/1998
JP     2001-099761 A   4/2001
(Continued)

OTHER PUBLICATIONS

PCT/JP2012/079865 Written Opinion dated Nov. 12, 2012.

*Primary Examiner* — Robert Clemente
(74) *Attorney, Agent, or Firm* — Hahn Loeser & Parks LLP

(57) ABSTRACT

The present invention provides a method and apparatus for rapidly extracting the analyte existing in the liquid phase in analyzing an analyte "having a large partition coefficient in gas-liquid equilibrium", "having a high water solubility", or "having a low olfactory threshold" by a gas-liquid contact extraction method, and further provides, a method and apparatus for unmanned continuous sample introduction of the analyte to a GC or the like for a long time. In the present invention, using a gas-liquid contact extractor to which a sample liquid is continuously introduced from above and a purge gas from beneath, the analyte in the sample liquid is extracted by gas-liquid contact between the sample liquid and the purge gas. A discharge pipe is connected to the bottom of the gas-liquid contact extractor, the pipe having a liquid sump through which the sample liquid is discharged, while blocking the outflow of the purge gas from the liquid sump.

12 Claims, 16 Drawing Sheets

(51) Int. Cl.
G01N 30/02 (2006.01)
G01N 1/40 (2006.01)
G01N 30/72 (2006.01)

(52) U.S. Cl.
CPC .... *G01N 30/7206* (2013.01); *G01N 2001/4066* (2013.01); *G01N 2030/025* (2013.01); *G01N 2030/065* (2013.01)

(56) References Cited

FOREIGN PATENT DOCUMENTS

| | | |
|---|---|---|
| JP | 2002-062256 A | 2/2002 |
| JP | 2002-177944 A | 6/2002 |
| JP | 2003-215042 A | 7/2003 |
| JP | 2005-003387 A | 1/2005 |

GAS-LIQUID CONTACT EXTRACTION METHOD AND APPARATUS

TECHNICAL FIELD

The present invention relates to a method and apparatus for efficiently gas-liquid extracting a dissolved substance in a liquid (hereinafter referred to as "analyte") in analysis thereof by using a gas chromatograph (hereinafter referred to as "GC" in some cases) or a gas chromatograph mass spectrometer (hereinafter referred to as "GC/MS" in some cases).

BACKGROUND ART

Examples of the analytical, method using gas-liquid extraction operation in analysis by a GC or GCMS include a purge-and-trap method (hereinafter referred to as "P & T" in some cases) and a head space method (hereinafter referred to as "HS" in some cases). These analysis methods are described in the water supply law under the authority of the Ministry of Health, Labor and Welfare.

(1) P & T Method and Problems Thereof

In P & T method, a gas having a small solubility in a solution is flowed so that an analyte dissolved in the solution is forced to be extracted into the gas phase. The extracted analyte is temporarily retained on an adsorbent for condensation of the analyte. Subsequently, the adsorbent is rapidly heated for desorption of the heated analyte from the adsorbent. The analyte is then introduced to the GC analytical column.

In extraction of an analyte from water by P & T method, the purging efficiency R in the ideal state can be obtained by Equation 1.

$$R = \frac{m_a}{m_0} = 1 - \exp\left[\frac{-F \cdot t}{K \cdot V_L + V_G}\right] \quad \text{(Equation 1)}$$

In Equation 1, F represents the purge gas flow rate, t represents the purge time, K represents the partition coefficient, $V_L$ represents the volume of a sample, $V_G$ represents the volume of gas phase in a vessel, $m_0$ represents the amount of analyte in an original solution, and $m_a$ represents the amount of analyte out in the gas phase.

The larger the partition coefficient is, the higher total purge flow rate is required to increase the recovery rate. In the subsequent step of retaining the extracted analyte in the purge gas on an adsorbent, it is required to consider the total flow rate of the purge gas, since the adsorbent for use has a breakthrough volume for each analyte.

From Equation 1, it can be understood that the purging efficiency is increased by increasing the purge gas flow rate, reducing the partition coefficient K, reducing the volume of a sample, and reducing the gas phase portion in a purge vessel.

Problems of P & T Method

1) Recovery Rate of Water-Soluble Component Having a Large Partition Coefficient In P & T method, even with an increased total purge flow rate, non polar components with a small partition coefficient coexisting in water are mainly recovered, so that it is difficult to improve the recovery rate of a water-soluble component having a large partition coefficient K.

It is said that a musty odor component in tap water has a threshold of 1 ppt. In other words, a man recognizes musty odor of an analyte even when it exist in an amount of 1 pg in 1 ml of tap water. It is said that trichloroanisole formed from phenols and the residue due to sterilization with hypochlorous acid has an olfactory threshold of 0.03 ppt. On the other hand, measurement sensitivity of GC/MS cannot reach the level of human sensitivity. Though depending on the amount of contaminants not to be measured or the like, several pg of analyte is required to be introduced to a separation column of GC so as to reach the mass analysis part for the detection of analyte.

In the measurement methods including P & T method and HS method, use of 20 ml of sample water is recommended in analysis (corresponding to 20 pg for a musty odor component concentration of 1 ppt).

At a sample extraction temperature of 40° C., although 100% of benzene can be recovered with a total purge gas flow rate of 800 ml, only 21.8% of 2-MIB and 21.4% of Geosmin can be recovered. Further, an increased total purge gas flow rate for the purpose of improving the recovery rate of an analyte having a large partition coefficient without consideration of the breakthrough volume of an adsorbent causes breakthrough of the analyte. In other words, there exists the upper limit for the total purge gas flow rate depending on the adsorbent for use (Table 1).

TABLE 1

Extraction efficiency with an amount of the sample of 20 mL and a vessel having a space volume of 20 mL
Purge flow rate of 20 ml/min

|  | Temperature (° C.) | Partition coefficient K | Total purge flow rate (ml) 400 | 800 | 1600 |
|---|---|---|---|---|---|
| Benzene | 40 | 3.18 | 99.2% | 100.0% | 100.0% |
|  | 50 | 2.63 | 99.6% | 100.0% | 100.0% |
|  | 60 | 2.20 | 99.8% | 100.0% | 100.0% |
| MB | 40 | 161.50 | 11.6% | 21.8% | 38.9% |
|  | 50 | 101.62 | 17.7% | 32.3% | 54.1% |
|  | 60 | 65.75 | 25.9% | 45.1% | 69.8% |
| Geosmin | 40 | 164.75 | 11.4% | 21.4% | 38.3% |
|  | 50 | 96.12 | 18.6% | 33.8% | 56.1% |
|  | 60 | 57.93 | 28.8% | 49.3% | 74.3% |

2) Problems Caused by Increased Purge Flow Rate

The purge vessel of conventional P & T method causes scattering of liquid droplets as the purge flow rate is increased. In real samples, metal, rust, microbes, bacteria or the like deposit on the piping, causing a trouble in the apparatus. It is also said that bubbling of the sample by purging reduces the gas-liquid extraction efficiency. With a slow purge flow rate, the time for analysis is prolonged to increase the total purge gas amount (refer to Anal. Chem., 58 (1986) 1822, James F. Pankow).

3) Slow Mass Transfer of Analyte in Water to Gas Phase

It is considered that the reasons for needing time for gas-liquid equilibrium in P & T method include: a) homogenization of gas phase concentration in a bubble, b) mass transfer at the gas-liquid (bubble) interface, and c) mass transfer in water. The largest contribution comes from c).

It is therefore necessary to improve the contact efficiency between gas and liquid by making many small bubbles in a purge vessel so as to uniformly flow the bubbles in the purge vessel and increasing the gas-liquid contact area.

Installation of a sintered filter with a fine mesh, which is called frit, in the purge vessel is thus important. In real samples, however, fine particulate substances, algae or the like accumulated on the frit cause contamination of the samples, resulting in variation in the recovery rate and necessity of frequent maintenance of the frit or the like.

4) Cryofocus

Since P & T method has a poor extraction efficiency, cryofocusing with liquid nitrogen is employed to introduce all the amount of extracted analyte to a GC or GC/MS. In performing continuous automatic analysis for a 24-hour period in a water purification plant, work for supplying liquid nitrogen is required. And it is difficult to be fully automated, and resulting in disadvantage in analysis cost.

(2) HS Method and Problems Thereof

In HS method, a sample is enclosed in a hermetically sealed vial, heated at a constant temperature for a predetermined time, and kept warm for reaching a gas-liquid equilibrium state. Subsequently, a predetermined amount of gas phase portion is sampled and analyze.

Problems of HS Method

The concentration in gas phase by HS method can be obtained by Equations 2.

Concentration in gas phase $C_G = C_L^0/(K+\beta)$

Partition coefficient $K = C_L/C_G$

Phase ratio $\beta = V_G/V_L$ (Equations 2)

In the equations, $C_G$ represents the concentration (g/cm$^3$) of the analyte in gas phase, $C_L$ represents the concentration (g/cm$^3$) of the analyte in liquid phase, $V_G$ represents the volume of gas phase, $V_L$ represents the volume of liquid phase, and $C_L^0$ represents the concentration of a sample before reaching equilibrium.

Based on Equations 2, in the case of a water-soluble component having a large partition coefficient K, an analyte to be extracted in the gas phase has a poor recovery rate. The partition coefficient K needs to be reduced to increase $C_G$. It is understood that raising the vial temperature, performing salting out operation (for a water sample), and addition of an acid or base are effective.

Meanwhile, reduction in β (increase in the amount of a sample or reduction of gas phase part) is not very effective in practice to improve the sensitivity.

Recently, a technique has been developed to increase the sensitivity of HS method, in which a portion of gas phase in gas-liquid equilibrium state is sampled multiple times from a sample vial and analyte is an adsorption tube and then desorbed by rapid heating for introduction to an analytical column (multiple HS method). The improvement of sensitivity for an analyte having a large partition coefficient K can be expected by the plural condensation in the multiple HS method. In addition to taking time in reaching gas-liquid equilibrium, however, the time required for sample pretreatment operation is increased due to the multiple sampling in the gas-liquid equilibrium state.

In the multiple HS method, the head space gas after reaching gas-liquid equilibrium is repeatedly condensed and collected at an adsorbent multiple times. In P & T method, gas-liquid equilibrium is made with microbubbles for continuous extraction. Although there is a difference in that HS method involves batch treatment and P & T method involves continuous extraction, HS method and P & T method are the same in principle, so that the amount of extraction depends on the partition coefficient.

The major problem of both is that although the gas concentration of analyte is high immediately after starting the extraction operation after introduction of a sample to a vessel or a purge vessel, since the partition coefficient (ratio of the concentration in solution to the concentration in gas) is constant, the concentration in the gas is reduced as the concentration of solution is reduced due to the extraction of the analyte from the solution. In other words, in the last half of extraction operation in P & T method, the amount of extraction of analyte is reduced in spite of consuming a large amount of extraction gas.

Gas-liquid countercurrent contact extraction is a gas-liquid extraction operation having potential to solve the problem of the conventional methods. The method is employed for removal or recovery of a predetermined component from a large amount of liquid in the chemical engineering field like plants or the like (refer to Japanese Patent Laid-Open No. 10-57947 and Japanese Patent No. 3006894).

In Japanese Patent Laid-Open No. Heisei 10-57947, a method for separating a large amount of ammonia is disclosed, in which an ammonia-containing solution is splashed into gas phase to be micronized for extreme enlargement of the gas-liquid contact area, so that the dispersion is performed with an enhanced emission efficiency of ammonia into gas phase. Accordingly, this method cannot be suitable for a method and apparatus for analyzing a small amount or trace of a sample.

In Japanese Patent No. 3006894, a structure with an erected pipe line bent in the vertical direction for flowing a liquid from above and a gas from beneath, and a structure with a pipe having an inner wall part with a wick for a liquid phase transfer by capillarity are disclosed.

When a pipe reactor (pipe line) indicated therein is tilted, the liquid does not contact with a filling material 6, resulting in insufficient gas-liquid contact surface area. Accordingly, a wick is arranged on the inner wall surface of a pipe, allowing for a liquid phase transfer of the liquid by capillarity. Although the liquid phase transfer by capillarity can be applied to a case having a large amount of liquid, the control of time is not effective in an analysis process for a trace of a liquid sample, and in the case that fine particles exist in the sample liquid, the fine particles deposited on a rotating member and the wick may cause contamination of the inner wall surface of the pipe. The liquid phase transfer by capillarity is, therefore, not suitable for continuous operation of the apparatus. Furthermore, in the case that a surfactant is contaminated in the liquid sample, or in the case that the liquid sample is a carbonated beverage, extraction of the sample itself may be difficult due to foaming in some cases, so that practical application cannot be achieved.

Literature "Analysis Sample Pretreatment Handbook" (by Masahiro Furuno, 2003, Maruzen Co., Ltd.) suggests the application of a gas-liquid contact extractor to GC analysis, flowing a sample liquid from above a helical pipe and sending a purge gas from beneath. However, the apparatus shown in the literature allows for reciprocal free flows of a sample liquid and purge gas only, without consideration of the control of the sample liquid and the purge gas and without consideration of the control of the relationship therebetween. Since the extraction efficiency between gas and liquid is extremely low due to the superficial mutual gas-liquid contact, so that it is difficult to use the extraction sample as an analysis sample. Practical application has not been achieved yet.

PRIOR ART

Patent Document

Patent document 1: Japanese Patent Laid-Open No. Heisei 10-57947
Patent document 2: Japanese Patent No. 3006894

Non Patent Document

Non Patent document 1: Anal. Chem., 58 (1986) 1822, James F. Pankow
Non Patent document 2: "Analysis Sample Pretreatment Handbook" (by Masahiro Furuno, 2003, Maruzen Co., Ltd.)

DISCLOSURE OF THE INVENTION

Problems to be Solved by the Invention

In view of the importance of how to rapidly transfer an analyte having a large partition coefficient and a small olfactory threshold existing in a liquid phase to a gas phase in GC or GC/MS analysis, it is necessary to obtain a method and apparatus for allowing the concentration of analyte in the gas phase portion at the outlet of purge gas to reach close to a theoretical value for use of gas-liquid contact extraction. With clarification of the method and apparatus, the extraction efficiency of an analyte equivalent to a theoretical value can be obtained and cryofocus is not required. It is thus required to obtain a method and apparatus allowing for fully automated analysis in GC or GC/MS analysis of a sample sampled from a water purification plant or the like.

In P & T method and HS method, analysis is performed by using a liquid sample collected in a given space, so that continuous supply and analysis of the sample over a long period of time cannot be made. In, for example, monitoring the analyte in tap water, the analyte in river water, or the analyte in a sample liquid for quality control or the like in a beverage manufacturer, manual sampling of a predetermined amount is required for analysis as time goes by. A sample introduction apparatus for performing continuous unmanned sampling and introduction of the sample to a GC or GC/MS for a 24-hour period is therefore required.

In addition, there exists an increase in demand for unmanned continuous 24-hour sampling and introduction of the samples to GC or GC/MS, particularly for an analyte "having a large partition coefficient in gas-liquid equilibrium", "having high water solubility", or "having a low olfactory threshold". The analysis of an analyte "having a large partition coefficient in gas-liquid equilibrium", "having high water solubility", or "having a low olfactory threshold" by using a GC or GC/MS is, however, difficult by the conventional P & T method or HS method.

Means for Solving the Problems

In order to solve the above problems, a method and apparatus for continuously supplying a sample liquid to a gas-liquid extraction portion, ensuring the supply balance between the sample liquid and purge gas, rapidly mass-transferring an analyte into the gas phase, guiding the analyte to a collecting pipe and introducing a sample to a GC or GC/MS is required. In other words, a method and apparatus for performing extraction in all the time during continuous flow of the sample is required.

Furthermore, for continuous GC or GC/MS analysis for a long period, a method and apparatus which eliminate manual operation such as supply of liquid nitrogen for cryofocusing and solve the problems of P & T method and HS method such as recovery of a component having a large partition coefficient and prolonged treatment time is required. In other words, a method and apparatus for performing extraction in all the time during continuous flow of the liquid sample is required.

The present invention therefore provides a gas-liquid contact extraction method using a gas-liquid contact extractor to which a sample liquid is continuously introduced from above and a purge gas from beneath, for extracting an analysis species in the sample liquid by gas-liquid contact between the sample liquid and the purge gas. While the sample liquid is discharged through a liquid sump provided to a discharge pipe connected to the bottom of the gas-liquid contact extractor, the outflow of the purge gas from the liquid sump is blocked.

Further, the gas-liquid contact extraction method is provided, wherein the sample liquid is preheated to the extraction temperature in the gas-liquid contact extractor prior to supplying the sample liquid to the gas-liquid contact extractor.

Further, the gas-liquid contact extraction method is provided, wherein a water-soluble component having a partition coefficient K larger than 1 or an analyte having an olfactory threshold lower than 10 ppt (pg/ml) existing in the sample liquid is gas-liquid contact extracted.

Further, the gas-liquid contact extraction method is provided, wherein the gas-liquid contact extractor is provided in a temperature-controlled oven, and the temperature of a flow channel to a collection tube for condensing the gas-liquid contact extracted analyte is set to a temperature equal to or higher than the oven temperature (gas-liquid extraction temperature), so that the gas-liquid extracted analyte is condensed in the collection tube.

Further, a gas-liquid contact extracting apparatus is provided, including a gas-liquid contact extractor to be supplied with a liquid sample from above and a purge gas from beneath. A discharge pipe is connected to the bottom of the gas-liquid contact extractor, and a liquid sump provided to the discharge pipe for discharging the sample liquid and blocking the discharge of the purge gas.

Further, the gas-liquid contact extraction apparatus is provided, wherein the contact surface of the gas-liquid contact extractor with a sample liquid is surface treated to achieve a spread wetting state.

Further, the gas-liquid contact extraction apparatus is provided, wherein the surface treatment is any one of a hydrophilic treatment and a water repellent treatment.

Further, an automatic liquid sample supply apparatus including a liquid sample supply part connected to the gas-liquid contact extraction apparatus through a syringe pump and a selector valve for switching a flow channel is provided, allowing an analyte gas-liquid contact extracted by the gas-liquid contact extraction apparatus to be sent to a collection tube.

Advantages of the Invention

According to the present invention, a liquid sample is supplied to a gas-liquid contact extractor at the extraction temperature, so that the gas-liquid contact at a gas-liquid interface can be sufficiently and rapidly performed. As a result, the gas-liquid equilibrium of the liquid sample is achieved in a short time, so that an analyte can be rapidly and reliably secured.

Further, a liquid sump arranged in the discharge portion of the sample liquid prevents the purge gas from discharging from the discharge portion. Adjusting the amount of supply of the sample liquid, the purge gas pressure, and the purge gas flow rate to the gas-liquid contact extractor allows the gas-liquid contact ratio to be increased. Consequently, the extraction efficiency of the analyte is increased, and further, the flow of analyte in a predetermined amount is reliably sent to a condensation pipe or the like.

In addition, the liquid sump installation allows the concentration of the analyte in a gas phase portion to reach close to the theoretical value. Consequently, an analyte having a large partition coefficient, having high water solubility, or having a low olfactory threshold can be easily analyzed, which has been conventionally difficult.

Furthermore, in monitoring the analyte in tap water, in river water, or in a sample liquid for quality control in a beverage, unmanned sample introduction including sampling, extraction, and analysis can be continuously performed without manual operation for a long time.

BRIEF DESCRIPTION OF DRAWINGS

FIG. 4 is a chromatogram in a reproducibility test with Geosimin and 2-MIB passing through.

DESCRIPTION OF EMBODIMENTS

Figure 1:
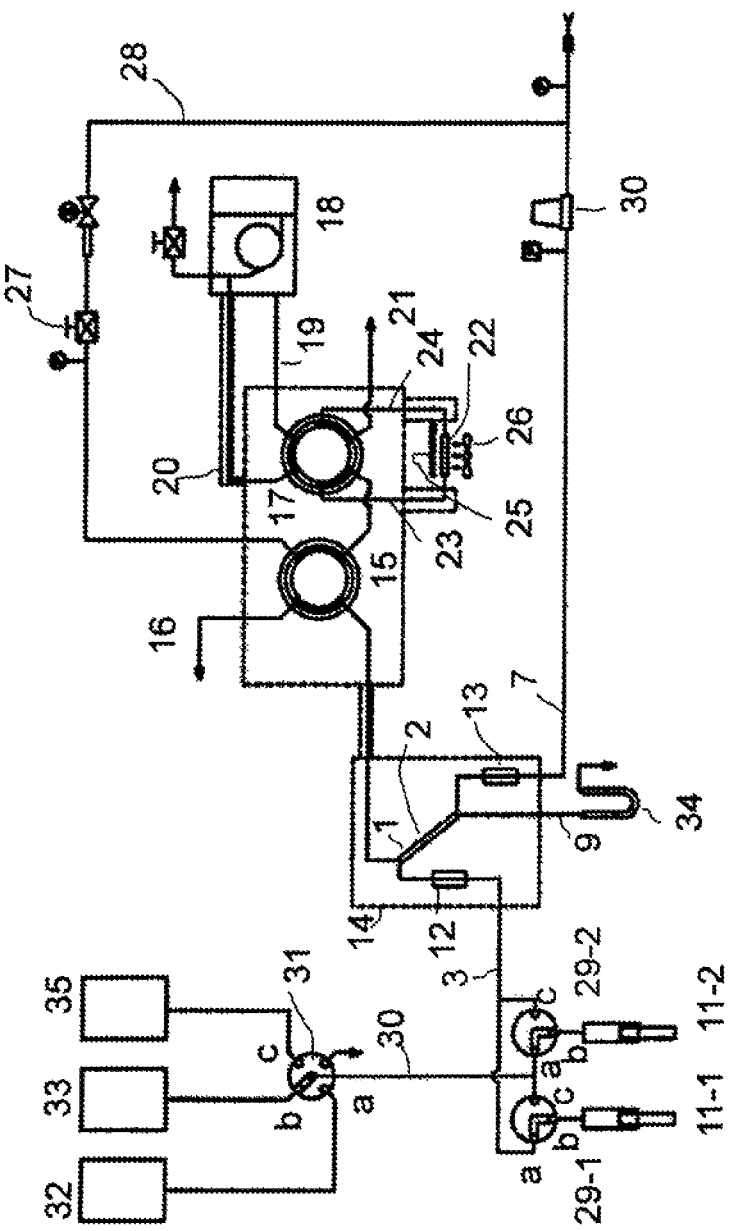
FIG. 1 is a schematic view illustrating a system configuration including an automatic liquid sample supply apparatus of the present invention.

An embodiment of the present invention is described below with reference to the drawings. FIG. 1 is a block diagram illustrating an example of a system 500 for use in quality control or the like of tap water or in a beverage plant, in which river water, tap water, or even a liquid supplied by flow from a supply source such as a large storage tank is connected on line for GC or GC/MS analysis. The system 500 includes a gas-liquid contact extractor 2, a gas-liquid contact extraction apparatus 200, and an automatic liquid sample supply apparatus 100 of the present invention so as to perform a gas-liquid contact extraction method of the present invention. A pipe 1 constituting the main body of the gas-liquid contact extractor 2 is disposed inclined. Preferably the pipe 1 is formed of a spiral pipe. Alternatively, the pipe 1 may be formed of a straight pipe or bent pipe etc.

The automatic liquid sample supply apparatus 100 includes the gas-liquid contact extractor 2 and the gas-liquid contact extraction apparatus 200. The gas-liquid contact extractor 2 is formed of glass, metal, or synthetic resin etc. for example, having an inner diameter of 3 to 10 mm and an inclination angle of 15° to 45° to the horizontal level. The length and the winding diameter of the gas-liquid contact extractor 2 formed of spiral pipe is not specifically limited, but preferably is 500 to 1,500 mm in length and 50 to 200 mm in winding diameter.

The contact surface of the gas-liquid contact extractor 2 with a sample liquid, i.e. the inner surface of the gas-liquid contact extractor 2, is preferably surface treated to improve the "wettability" on contact with the sample liquid, such that the gas-liquid contact surface area is enlarged in a so-called "spread wetting" state. Examples of the wetting mode with liquid on the inner surface of the gas-liquid contact extractor 2 include spread wetting, immersion wetting, and adhesion wetting as described in chronological scientific tables. Among these, preferably spread wetting is selected, allowing liquid to spread thinly.

In the case that the surface treatment for improving the wettability is required, the type of treatment is different depending on the sample. A hydrophilic treatment is performed for a water-based sample such as river water, tap water, a soft drink, and alcohol, while a water-repellent treatment is performed for an oil-based sample such as vegetable oil, and industrial oil.

For the hydrophilic treatment, superhydrophilization by plasma treatment, superhydrophilization by sol-gel method, superhydrophilization by a photocatalyst, superhydrophilization by an additive, superhydrophilization by coating with an inorganic nanoparticles, hydrophilization by hot water treatment of a gel film, hydrophilization by graft copolymerization, hydrophilization by hydrophilic micelle cross-linking, hydrophilization by corona discharge, hydrophilization by laser irradiation, and a treatment with hydrochloric acid etc. can be used.

For the water-repellent treatment, for example, techniques such as super water-repellency prepared by plasma treatment, super water-repellency prepared by fluorine-based surface modifiers, super water-repellency prepared by a chemical adsorption method, super water-repellency prepared by sol-gel method, super water-repellent treatment prepared by electrodeposition coating with addition of fluorine-based graft copolymer/fluorine-based resin fine particles, water-repellency prepared by a silane coupling agent, super water-repellency prepared by an acrylic silicone/silica composite film, water-repellency prepared by chemical adsorbed monomolecular film, super water-repellency prepared by ion beam modification, and techniques such as coating with a chemical substance having a functional group such as a saturated fluoroalkyl group (trifluoromethyl group, in particular), an alkyl silyl group, a fluoro acyl group, and a long-chain alkyl group can be used. The technique for use is selected according to each sample.

At the upper end of the pipe 1, an opening 4 for connecting a sample supply pipe 3 for supplying a sample liquid to the pipe 1, and an opening 6 for connecting a purge gas discharge pipe 5 to the pipe 1 are provided. Further, at the lower end of the pipe 1, an opening 8 for connecting a purge gas supply pipe 7 having a pressure controller 30 to the pipe 1, and an opening 10 for connecting a discharge pipe 9 for discharging the sample liquid to the pipe 1 are provided.

To the gas-liquid contact extractor 2 having the openings 4, 6, 8 and 10, a purge gas such as helium is sent through the gas supply pipe 7 and the opening 8 from beneath, and a sample liquid falls from above through the sample supply pipe 3 and the opening 4. The gas phase (purge gas) and the liquid (sample liquid) are contacted with each other in a countercurrent flow manner there so that the analyte existing in the liquid phase is rapidly transferred to the gas phase.

The sample supply pipe 3 communicates with a syringe pump 11. A predetermined amount of the sample liquid calibrated with the syringe pump 11 is supplied to the gas-liquid contact extractor 2 through a selector valve 31 and the sample supply pipe 3. The sample supply pipe 3 is provided with a preheat pipe 12. The gas supply pipe 7 is also provided with a preheat pipe 13. The gas-liquid contact extractor 2 is installed in an oven 14 so as to be temperature controlled.

The purge gas discharge pipe 5 communicates with a valve 15. The valve 15 is connected to a vent 16 and a second valve 17. The valve 17 is provided with channels 19 and 20 for connecting with a GC or GC/MS 18, a vent 21, and channels 23 and 24 for connecting to a condensation pipe 22. A heater 25 and a fan 26 are installed opposite to the condensation pipe 22.

A connecting pipe 28 is connected to the valve 15. The connecting pipe 28 is connected to the gas supply pipe 7 through a needle valve 27. A predetermined number of sample tanks 32 are connected to the syringe pump 11 through a line 30 and the selector valve 31.

Preferably the automatic liquid sample supply apparatus 100 is provided with a gas-liquid contact extraction apparatus. The gas-liquid contact extraction apparatus includes the gas-liquid contact extractor 2, the discharge pipe 9 for discharging the sample liquid, and a liquid sump 34. The liquid sump 34 is a mechanism for maintaining a constant liquid level so as to block the purge gas from flowing out from the discharge pipe 9 connected to the bottom of the gas-liquid contact extractor 2. The liquid sump 34 is provided to the discharge pipe 9. A mechanism based on the principle of U-pipe manometer such as a U-pipe structure or a structure having a large-diameter portion may be used for the liquid sump 34 to temporarily reserve the sample liquid flowed out from the discharge pipe 9.

Alternatively, the liquid sump 34 may include piping connected to the opening 10 of the gas-liquid contact extractor 2 or the discharge pipe 9 for discharging the sample liquid instead of the monometer, at which a liquid level sensor and a solenoid valve (not shown) are installed for the discharged sample liquid to maintain a constant liquid level in the piping. Alternatively, a load corresponding to the water column may be imparted to the discharge portion of the U-pipe, such that the sample liquid can maintain the water level in the piping.

In the following, the operation of the gas-liquid contact extractor 2, the gas-liquid contact extraction apparatus 200, and the automatic liquid sample supply apparatus 100 are described. The sample liquid is supplied to the gas-liquid contact extractor 2 through the selector valve 31 and the sample supply pipe 3, by the syringe pump 11. The sample liquid is heated to the sample extraction temperature in the sample supply pipe 3 by the preheat pipe 12 so as to rapidly achieve a gas-liquid equilibrium state in the gas-liquid contactor extractor 2.

The flow channels of the entire system, particularly the flow channels in the oven 14 for housing the gas-liquid contactor extractor 2 and between the oven 14 and the GC or GC/MS 18, are temperature controlled to a temperature preferably equal to or higher than the sample extraction temperature. The temperature setting prevents the water vapor caused by the following purging from condensing and an analyte from being adsorbed.

The vessel 32 contains the sample liquid. The vessels containing a different sample liquid may be arranged in parallel so as to be each connected to the selector valve 31. A vessel 33 contains a reference sample liquid including an analyte with a known concentration. A vessel 35 contains washing water.

Subsequently, the operation of the automatic liquid sample supply apparatus 100 to supply a sample liquid to the gas-liquid contact extractor 2 is described. Firstly, the selector valve 31 is activated to open a port a connected to the vessel 32 which contains the sample liquid. Subsequently, a valve 29-1 moves to a position for connecting a port b with a port c, and a valve 29-2 moves to a position for connecting a port a with a port b. The vessel 32 which contains the sample liquid is thus connected to the piping 30, allowing the sample liquid to be sucked in with a syringe pump 11-1 and a syringe pump 11-2.

After completion of suction of the sample liquid with the syringe pump 11-1 and the syringe pump 11-2, the syringe pump 11-1 moves to a position for connecting a port a with the port b of the valve 29-1, so as to supply the sample liquid to the gas-liquid contact extractor 2 through the piping 3. On this occasion, the syringe pump 11-2 halts the operation for supplying the sample liquid. Prior to exhaustion of the sample liquid supplied by the syringe pump 11-1, the valve 29-1 moves to a position for connecting the port b with the port c so as to suck the sample liquid again.

While the syringe pump 11-1 sucks the sample liquid, the move to the position for connecting the port b with a port c of the valve 29-2 allows the sample liquid sucked with the syringe pump 11-2 to be supplied to the liquid contact extractor 2 from the piping 3.

As described above, the syringe pump 11-1 and the valve 29-1, and the syringe pump 11-2 and the valve 29-2 work together so as to continuously supply the sample liquid to the gas-liquid contact extractor 2.

The liquid sample warmed in the sample supply pipe 3 to be adapted to the extraction temperature enters the gas-liquid contact extractor 2 from the normally opened opening 4, and flows down along the bottom surface of the pipe 1 which is disposed inclined. On the other hand, the purge gas is supplied to the gas-liquid contact extractor 2 at a constant flow rate, warmed to a proper temperature by the preheat pipe 13 in the gas supply pipe 7, and continuously enters the gas-liquid contact extractor 2 from the opening 8 at the bottom so as to rise up. The sample liquid and the purge gas are thus contacted with each other in the counter current flow all the time.

The permeable flow rate of the sample liquid is 0.01 to 5 ml/min. The flow rate of the purge gas is 0.1 to 100 ml/min. The extraction temperature is set to a temperature suitable for extraction of an analyte within a range causing no freezing of the liquid sample and no thermal decomposition of the target analyte. The extraction time is set according to the liquid sample.

The gas and liquid phases warmed in the gas-liquid contact extractor 2 has a boundary where mass transfer is performed all the time. Improvement of contact efficiency between the gas and liquid, and rapidly transfer of the substance in the liquid, i.e. analyte, to the gas phase by the gas-liquid contact is required.

From the gas-liquid contact extractor 2 to which the sample liquid is supplied at a constant flow rate, the sample liquid is discharged through the liquid sump 34 based on the principle of U-pipe manometer all the time. The warmed liquid blocks the purge gas from flowing out from the liquid sump 34. As a result, the supply of the purge gas at a constant flow rate to the condensation pipe 22 for condensing the gas-liquid extracted analyte is secured. The pressure of purge gas is adjusted to a level required to supply the purge gas including extracted analyte to the condensation pipe 22 at a constant flow rate.

The sample liquid which is retained in the liquid sump 34 to be discharged blocks the purge gas from flowing out from the bottom of the gas-liquid contact extractor 2, so that the supply pressure of the purge gas can be maintained. Consequently, stable supply of gas phase is achieved in the gas-liquid contact extractor 2, balancing with the supply of the sample liquid. Sufficient gas-liquid contact can be thus achieved, contributing to the gas-liquid equilibrium.

Figure 2:
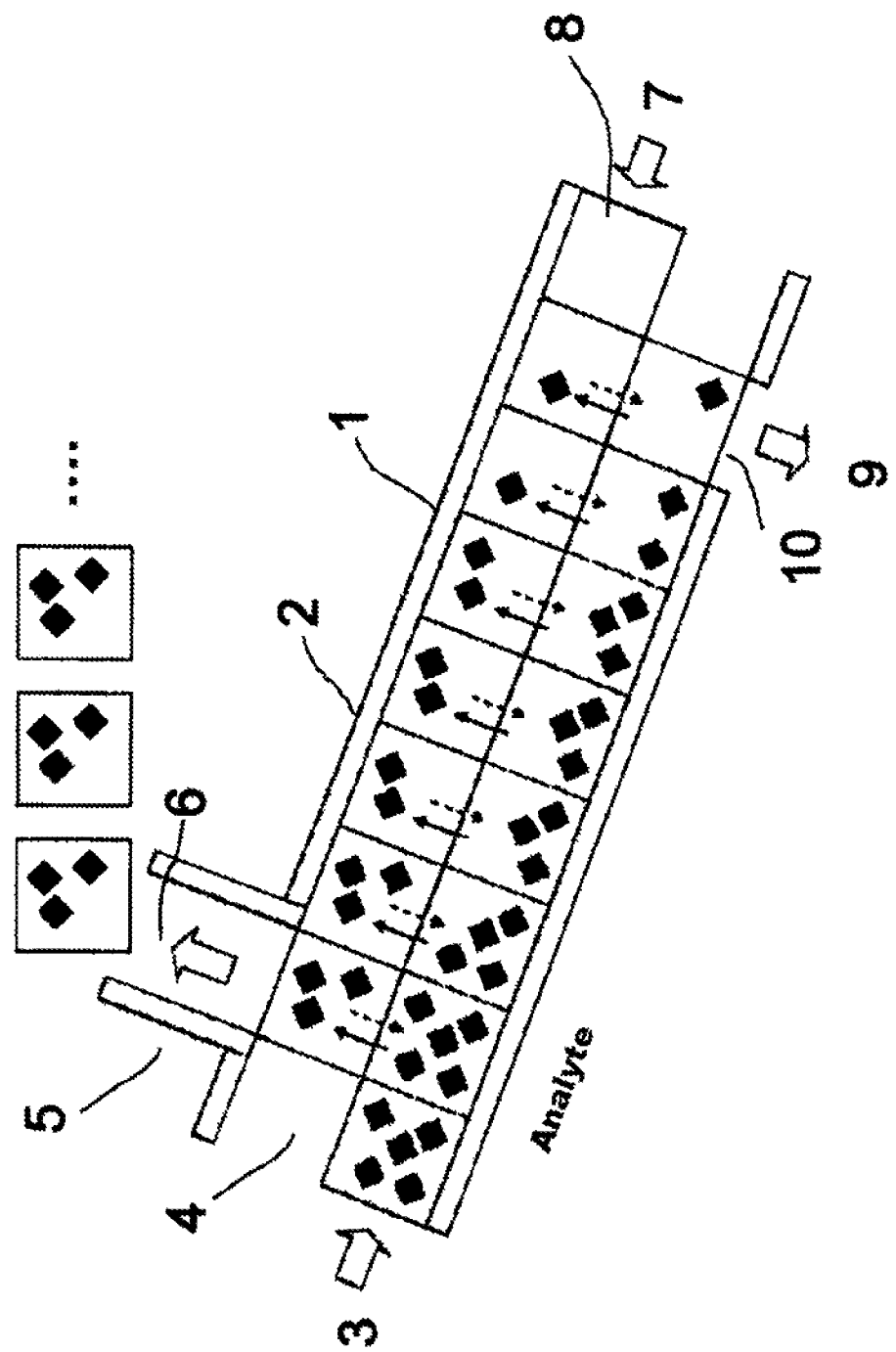
FIG. 2 is a diagram illustrating transfer state in gas-liquid equilibrium of an analyte.

The rapid approach to gas-liquid equilibrium in the vicinity of the opening 6 for connecting the purge gas discharge pipe 5 is the most important. The flows of gas phase and liquid phase and mass transfer of an analyte by countercurrent contact are schematically illustrated in FIG. 2. Due to the mass transfer between the gas phase and the liquid phase described above, the analyte is efficiently transferred into the gas phase as the sample liquid flows down. Consequently, the concentration of the analyte in the liquid phase is the smallest at the discharge outlet 10 of the liquid phase and the concentration of the analyte in the gas phase is the largest in the vicinity of the opening 6.

In the following Table 2 of Example 1, the theoretical values and the experimental values are described for conventional P & T method and the present invention. In the conventional P & T method, the difference between the theoretical value and the experimental value is large, proving that the mass transfer of the analyte to the gas phase is insufficient. In the present invention, the theoretical value matches the experimental value, proving that the gas-liquid equilibrium is achieved in the vicinity of the opening 6.

In the case that the gas-liquid equilibrium state is achieved at the outlet opening 6 for connecting the purge gas discharge pipe 5 in the gas-liquid contact extractor 2, the amount of the analyte to be transferred to the gas phase portion can be calculated based on Equation 2 which defines the partition coefficient. The partition coefficient is shown in Equation 2, which means that if $K=1$, "the concentration of sample compound in liquid phase ($g/cm^3$)" is equal to "the concentration of sample compound in gas phase ($g/cm^3$)." In other words, a compound having $K=1$ or more in the Table 1 exists more in the liquid phase than in the gas phase. In the present application, "the partition coefficient is large or small" means "K is larger than or smaller than 1".

In order to efficiently approach the theoretical gas phase concentration based on the gas-liquid equilibrium as close as possible in the gas-liquid contact extractor 2, it is important to reduce the thickness of liquid phase. As described above, the liquid phase has a thin thickness due to the wettability at the inner surface of the pipe 1 constituting the gas-liquid contact extractor 2.

Mass transfer in the liquid phase is governed by the diffusion coefficient. It is known that the diffusion coefficient of a molecule in water is in the order of about $10^{-5}$ $cm^2/sec$. The thinner the thickness of a liquid phase, the faster the time a transferred substance, i.e. analyte, reaches the gas-liquid interface, so that the number of times the analyte in the liquid phase comes in contact with the gas phase is increased. In other words, the thinner the thickness of the liquid phase, the larger amount of analyte transfers to the gas phase, meaning that the time for the gas-liquid equilibrium state to be achieved is shortened.

Benzene in a liquid phase having a flow thickness (depth) of 220 μm is brought under review in the following. Benzene has a diffusion coefficient in water of $1.02 \times 10^{-5}$ $cm^2/sec$. One benzene molecule in water exists somewhere in the range of 18 μm after one second. In the case of a liquid phase having a thickness of 0.22 mm (220 μm), the time required for reaching the liquid surface from the deepest bottom is about 10 seconds (12.2 seconds according to calculation). In the case of 30-second falling in the pipe 1 with a water flow rate of 2 ml/min, the benzene molecule can reach the gas-liquid contact surface two times. Consequently, the one benzene molecule has chances for transferring to the gas phase two times.

The flow of the liquid and the thickness of the water channel in the pipe 1 can be analyzed by the rate theory of an open channel. In the case of spiral-shaped pipe 1, the fluid has an enhanced mixing effect (water replacement between the bottom and top) due to the occurrence of secondary flow, which is the driving force for efficient mass transfer from the liquid phase to the gas phase.

Alternatively, the gas-liquid contact extractor 2 may be, for example, a box-type water channel having a plane bottom surface. The gas-liquid contact extractor 2 is not limited to the pipe shape described above, as long as having a flow channel allowing the sample liquid to flow from upstream and the purge gas to be introduced from downstream, such that the introduced purge gas is not discharged to anywhere other than a collection tube.

In the present invention, the partition coefficient K can be reduced by preheating of the sample liquid, and the liquid phase can be thinly formed due to the wettability of the inner surface of the pipe 1. Consequently, the rapid mass transfer of the analyte to the gas phase can be achieved, resulting in an increased purging efficiency. As a result, the concentration of the analyte in the gas phase theoretically calculated based on the definition of partition coefficient (Equation 2)(theoretical value) approximately matches the concentration of the analyte obtained in the actual experiment (experimental value).

Example 1

A sample water which contains 2-MIB and Geosimin was analyzed by a conventional P & T method and the gas-liquid contact extraction method of the present invention using a system including the gas-liquid contact extraction apparatus and the automatic liquid sample supply apparatus of the present invention shown in FIG. 1. Experimental examples for comparison of the amounts of 2-MIB and Geosimin mass transferred to the gas phase are shown in the following.

TABLE 2

| Item | | Method of the present application (average of 6 measurements) | Conventional P & T method (average af 3 measurements) |
| --- | --- | --- | --- |
| Parameter for extraction | Target setting value of purge gas flow rate at collection tube outlet (ml/min) | 80 | 80 |

TABLE 2-continued

|  | Item | Method of the present application (average of 6 measurements) | Conventional P & T method (average af 3 measurements) |  |
|---|---|---|---|---|
|  | Measured value of purge gas flow rate at collection tube outlet (ml/min) | 78.88 | 77.88 |  |
|  | Theoretically obtained saturated water vapor volume to be transferred to collection tube (ml) | 142.22 | 140.42 |  |
|  | Amount of purge gas amount corrected with amount of saturated water vapor at collection tube outlet (ml) | 1719.8 | 1698.02 |  |
|  | Purging time (=sampling time) (min) | 20 | 20 |  |
|  | Purge gas flow rate corrected with amount of saturated water vapor at collection tube outlet (ml/min) | 85.9 | 84.9 |  |
|  | Pressure in vessel (KPa) | 120 | 120 |  |
|  | Sample water flow rate (ml/min) | 2 | — |  |
|  | Total amount of sample water (ml) | 40 | 20 |  |
|  | Sample concentration (ppt) | 5 | 5 |  |
|  | 2-MIB content (pg) | 200 | 100 |  |
|  | Geosmin content (pg) | 200 | 100 |  |
|  | Oven temperature (° C.) | 60 | 80 |  |
|  | 2-MIB partition coefficient K | 65.75 | 65.75 |  |
|  | Geosmin partition coefficient K | 57.93 | 57.93 |  |
| Theoretical value of the method of present application | Theoretical amount of 2-MIB transferred to gas phase (pg) | 132.1 | 72.0 | Theoretical value of |
|  | Theoretical amount of Geosmin transferred to gas phase (pg) | 150.0 | 76.3 | conventional P & T method |
| Experimental value of the method of present application | Amount 2-MIB transferred to gas phase, obtained from experiment (pg) | 139.6 | 44.6 | Experimental value of |
|  | Amount of Geosmin transferred to gas phase, obtained from experiment (pg) | 167.2 | 59.9 | conventional P & T method |

In Table 2, the theoretical amounts of mass transfer of 2-MIB and Geosimin transferred from a liquid phase with a concentration of 5 ppt (5 pg/mL) to a gas phase and the respective extraction efficiencies for the conventional P & T method and the gas-liquid contact extraction method of the present invention. In the conventional P & T method, the amount of sample water was 20 ml. In the method of the present invention, water flowed at a flow rate of 2 ml/min for 20 minutes, totaling 40 ml.

In the conventional P & T method, the theoretical amounts of mass transfer to the gas phase calculated from Equation 1 are 72.0 pg for 2-MIB and 76.3 pg for Geosimin, while the experimental values were 44.6 pg for 2-MIB and 59.9 pg for Geosimin. The experimental values are significantly lower than the theoretical values. This means that the mass transfer from the liquid phase to the gas phase in the conventional P & T method was not rapidly performed, so that the gas-liquid equilibrium state was not achieved.

In contrast, in the method of the present invention, the theoretical amounts of mass transfer to the as phase calculated from Equation 2 are 132.1 pg for 2-MIB and 150.0 pg for Geosimin, while the experimental values were 139.6 pg for 2-MIB and 157.2 pg for Geosimin. The experimental values were approximately equal to the theoretical values. This means that the mass transfer from the liquid phase to the gas phase in the method of the present invention was rapidly performed, so that the gas-liquid equilibrium state was achieved at the outlet of the purge gas.

It was proved that the "spiral pipe (counter-flow) method" based on the principle of the gas-liquid countercurrent contact extraction of the present invention allows the extraction efficiency to be achieved according to the theory. Furthermore, the method of the present invention allows for condensation by extending the operation time for the gas-liquid countercurrent contact extraction, as long as the breakthrough volume of the adsorbent for the analyte is not exceeded. Consequently, the detection sensitivity in GC or GC/MS analysis can be improved.

<Experimental Conditions>
(1) Extraction conditions for sample water
1) Extraction temperature of sample water: 60° C.
2) Sample water
   Conventional P & T: 20 ml;
   Flow rate in the method of the present invention: 2 ml/min
3) Purge gas flow rate
   Conventional P & T: 80 ml/min (120 kPa);
   Method of the present invention: 80 ml/min (120 kPa)
4) Extraction time: 20 min
5) Sample flow channel temperature: 60° C.
6) Spiral pipe made of Pyrex (registered trademark) glass
   Shape: Inner diameter of 4 mm and length of 1,200 mm;
Installation angle: 30 degrees
7) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collecting pipe: 3.2 mm I.D.×200 mm)
2) Temperature during collection: 60° C.
3) Collection tube heating temperature: 220° C. (10 minutes)
4) Desorption flow rate during heating: 11 ml/min
5) Valve temperature: 150° C.
6) Transfer line temperature: 150° C.

(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 min)-20° C./min-250° C. (5 min)
6) Capillary column: InertCap 5 MS/Sil, 0.25 mm I. D.×30 m, df=0.25 μm
7) Ion source: EI, 70 eV
8) SIM mode: 2-MIB: m/z 95, 107; Geosimin: m/z 112, 125

Example 2

The extraction efficiencies of 2-MIB and Geosimin of the gas-liquid contact extraction method of the present invention using the automatic liquid sample supply apparatus of the present invention were compared by changing the purge gas flow rate and sample water flow rate. The conditions for the comparison of extraction efficiency of 2-MIB and Geosimin due to the difference in the purge gas flow rate and the sample water flow rate are as follows:

A: sample water flow rate: 4 ml/min, purge gas flow rate: 160 ml/min, extraction time: 10 minutes;

B: sample water flow rate: 2 ml/min, purge gas flow rate: 80 ml/min, extraction time: 20 minutes;

C: sample water flow rate: 1 ml/min, purge gas flow rate: 40 ml/min, extraction time: 40 minutes.

Figure 3:
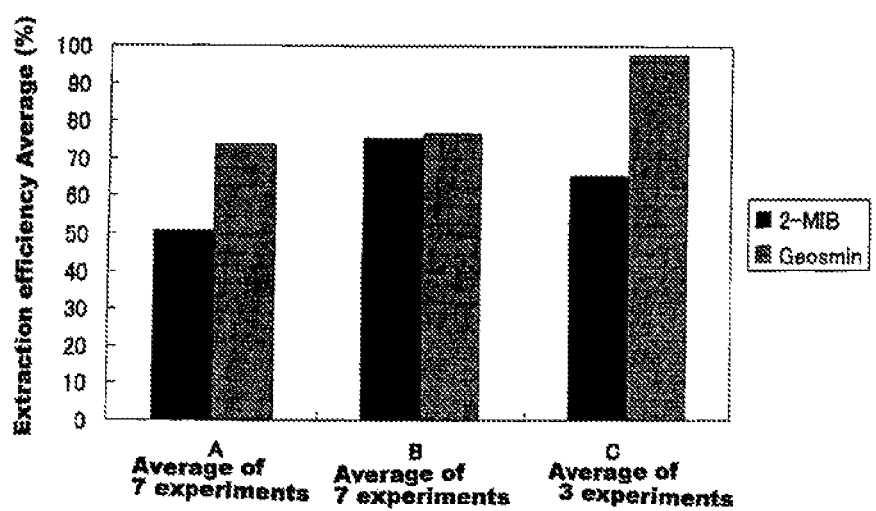
FIG. 3 is a comparison chart of extraction efficiency of 2-MIB and Geosimin due to difference in purge gas flow rate and sample water flow rate.

The extraction temperature was 60° C. The results are shown in FIG. 3. It was proved that B in the drawing achieved the conditions for both of the components to be obtained at a high extraction efficiency.

<Experimental Conditions>
(1) Extraction conditions for sample water
1) Extraction temperature of sample water: 60° C.
2) Sample water flow rate: 1, 2, and 4 ml/min
3) Purge gas flow rate: 40 ml/min (60 kPa), 80 ml/min (120 kPa), and 160 ml/min (240 kPa)
4) Sample flow channel temperature: 60° C.
5) Extraction time: 10, 20, and 40 min
6) Spiral pipe made of Pyrex (registered trademark) glass
    Shape: Inner diameter of 4 mm and length of 1,200 mm; Installation angle: 30 degrees
7) Inner surface treatment of spiral pipe:
    A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220° C. (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 mm)-20° C./min-250° C. (5 min)
6) Capillary column: InertCap 5 MS/Sil, 0.25 mm I. D.×30 m, df=0.25 μm
7) Ion source: EI, 70 eV
8) SIM mode: 2-MIB: m/z 95, 107; Geosimin: m/z 112, 125

Example 3

An experiment was performed to ensure the reproducibility of the analysis of 2-MIB and Geosimin by the system shown in FIG. 1 including the gas-liquid contact extraction apparatus and automatic liquid sample supply apparatus of the present invention. Geosimin and 2-MIB are known as substances causing musty odor in tap water. The water quality criteria according to the water supply law revised in April, 2004 set a low reference value of 0.01 μq/L (10 ppt) for the substances. An extremely low quantitative lower limit of 0.001 μg/L (1 ppt), which is 1/10 of the reference value, is further required. The olfactory threshold is described in "Olfactory Measurement Method Manual" by the Ministry of the Environment.

Figure 4:
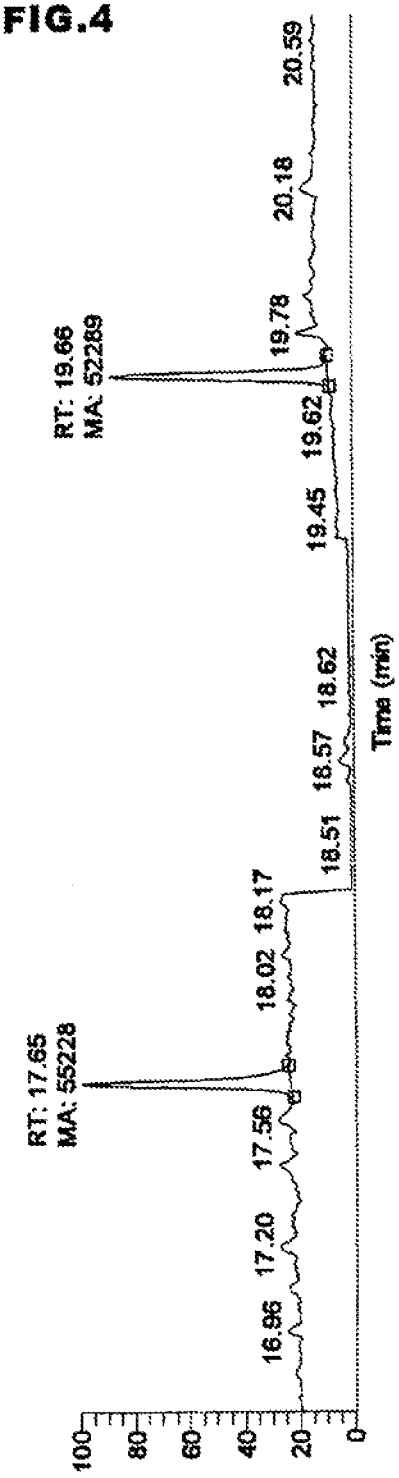
Figure 5:
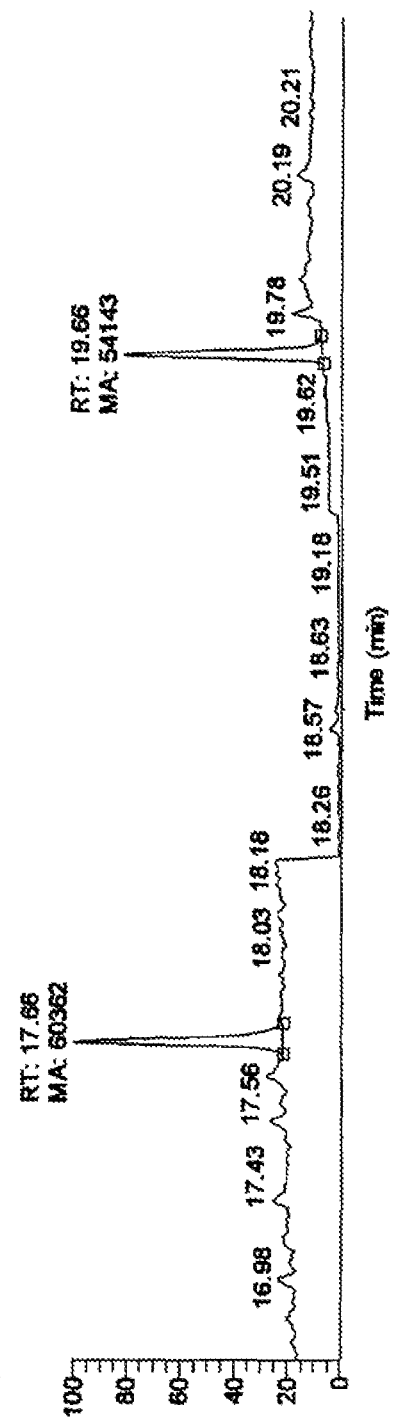
FIG. 5 The same as above.
Figure 6:
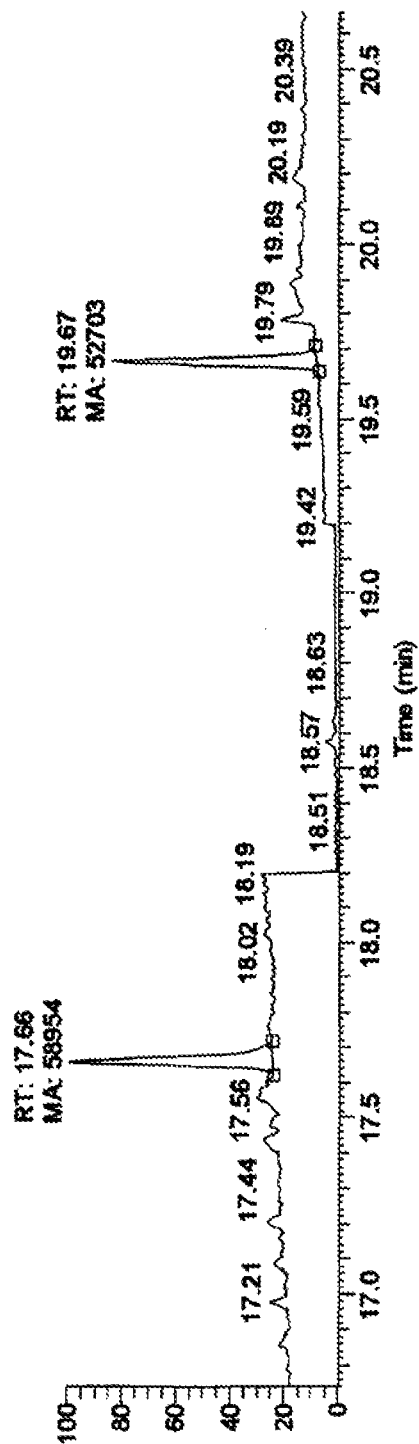
FIG. 6 The same as above.

Tests were repeated so check for reproducibility for 2-MIB and Geosimin each having a concentration of 1 ppt. The results are shown in FIG. 4, FIG. 5, and FIG. 6. Further, the CV (%) for the peak area value of 2-MIB and Geosimin measured three times was calculated. Good results were obtained as shown in Table 3.

TABLE 3

|         | First time | Second time | Third time | CV (%) |
|---------|------------|-------------|------------|--------|
| 2-MIB   | 55228      | 60362       | 58954      | 3.7    |
| Geosmin | 52289      | 54143       | 52703      | 1.5    |

<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)
4) Sample flow channel temperature: 60° C.
5) Extraction time: 20 min
6) Spiral pipe made of Pyrex (registered trademark) glass
    Shape: Inner diameter of 4 mm and length of 1,200 mm; Installation angle: 30 degrees
7) Inner surface treatment of spiral pipe:
    A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220 (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 min)-20° C./min-250° C. (5 min)
6) Capillary column: InertCap 5 MS/Sil, 0.25 mm I. D.×30 m, df=0.25 μm
7) Ion source: EI, 70 eV
8) SIM mode: 2-MIB: m/z 95, 107; Geosimin: m/z 112, 125

Example 4

Figure 7:
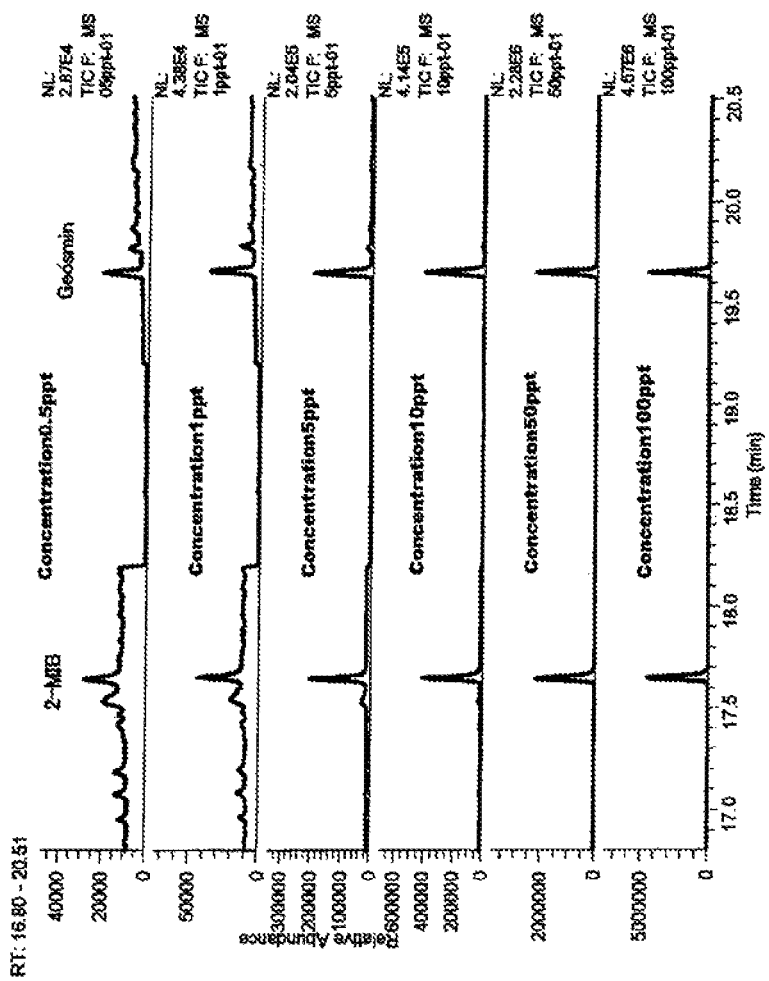
FIG. 7 is chromatograms in the same test as above with different concentrations.
Figure 8:
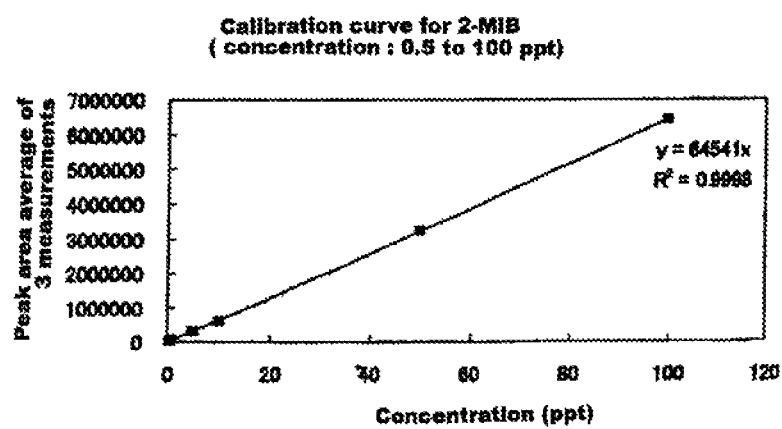
FIG. 8 is a resultant linear calibration curve for 2-MIB from the same test as above.
Figure 9:
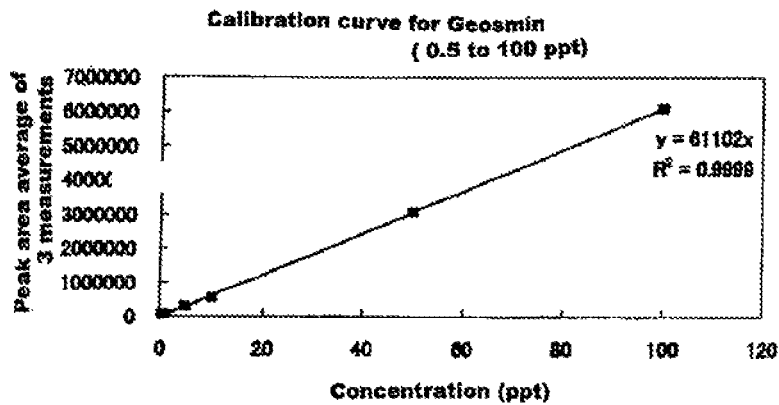
FIG. 9 is a resultant linear calibration curve for Geosimin from the same test as above.

The gas-liquid contact extraction method of the present invention using a system including the gas-liquid contact extraction apparatus and the automatic liquid sample supply apparatus of the present invention shown in FIG. 1 was performed as an experiment for examining the uniformity (linearity) of the extraction time due to difference in sample concentration of 2-MIB and Geosimin. The mass chromatograms for concentrations of 0.5 ppt, 1 ppt, 5 ppt, 10 ppt, 50 ppt, and 100 ppt are shown in FIG. 7 for examining the linearity for a concentration range from 0.5 to 100 ppt. The experiment was repeated three times, and the results are shown in FIG. 8 and FIG. 9, plotting the respective average values on the vertical axis and concentrations on the horizontal axis. Good linearity with $R^2=0.999$ or higher was obtained for both of 2-MIB and Geosimin.

(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 min)-20° C./min-250° C. (5 min)
6) Capillary column: InertCap 5 MS/Sil, 0.25 mm I. D.×30 m, df=0.25 μm
7) Ion source: 70 eV
8) SIM mode: 2-MIB: m/z 95, 107; Geosimin: m/z 112, 125

Example 5

It is said that 2,4,6-trichloroanisole (hereinafter referred to as TCA) has an extremely small olfactory threshold of 30 ppq.

TABLE 4

| | \multicolumn{9}{c}{Concentration (ppt)} | | | | | | | | |
|---|---|---|---|---|---|---|---|---|---|
| | \multicolumn{3}{c}{100 Peak area value of 3 measurements} | | | \multicolumn{3}{c}{50 Peak area value of 3 measurements} | | | \multicolumn{3}{c}{10 Peak area value of 3 measurements} | | |
| 2-MIB | 6430213 | 6488910 | 6478732 | 3179863 | 3190862 | 3291326 | 576878 | 587093 | 556576 |
| AVG | | 6465952 | | | 3220680 | | | 573516 | |
| CV (%) | | 0.40 | | | 1.56 | | | 2.21 | |
| Geosmin | 6000809 | 6262429 | 6103896 | 3001521 | 3015845 | 3116489 | 564322 | 564670 | 544758 |
| AVG | | 6122378 | | | 3044618 | | | 557917 | |
| CV (%) | | 1.76 | | | 1.68 | | | 1.67 | |
| | \multicolumn{9}{c}{Concentration (ppt)} | | | | | | | | |
| | \multicolumn{3}{c}{5 Peak area value of 3 measurements} | | | \multicolumn{3}{c}{1 Peak area value of 3 measurements} | | | \multicolumn{3}{c}{0.5 Peak area value of 3 measurements} | | |
| 2-MIB | 292772 | 285696 | 307680 | 57105 | 60910 | 56914 | 26336 | 27266 | 27493 |
| AVG | | 295383 | | | 58310 | | | 27032 | |
| CV (%) | | 3.10 | | | 3.16 | | | 1.85 | |
| Geosmin | 271943 | 269337 | 281126 | 52287 | 56618 | 52450 | 23833 | 24445 | 23026 |
| AVG | | 274136 | | | 53785 | | | 23758 | |
| CV (%) | | 1.84 | | | 3.73 | | | 2.44 | |

<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)
4) Sample flow channel temperature: 60° C.
5) Extraction time: 20 min
6) Spiral pipe made of Pyrex (registered trademark) glass
   Shape: Inner diameter of 4 mm and length of 1,200 mm;
   Installation angle: 30 degrees
7) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220 (10 minutes)
4) Desorption flow rate during heating: 11 ml/min
5) Valve temperature: 150° C.
6) Transfer line temperature: 150° C.

The compound is widely known as a substance causing musty odor, which is generated in the growth process of a kind of mold which o-methylates and detoxifies 2,4,6-trichlorophenol (hereinafter referred to as "TCP") as timber fungicide.

It has been reported that the contamination with TCA can occur during chlorine treatment of raw water or during transportation using a water distribution system in addition to the TCP contamination of timber. Strict control is thus required in manufacturing facilities which handle water, not only in water source.

Accordingly, 2,4,6-trichloroanisole having a concentration of 30 ppq was prepared and analyzed by the same gas-liquid contact extraction method as in Example 1, at a sample flow rate of 2 ml/min and for an extraction time of 100 minutes (total flow volume of 200 ml). MS measurement was performed in SIM mode. The monitor ion was set to m/z 210, 212. Other analysis conditions are the same as those in Example 1.

Figure 10:
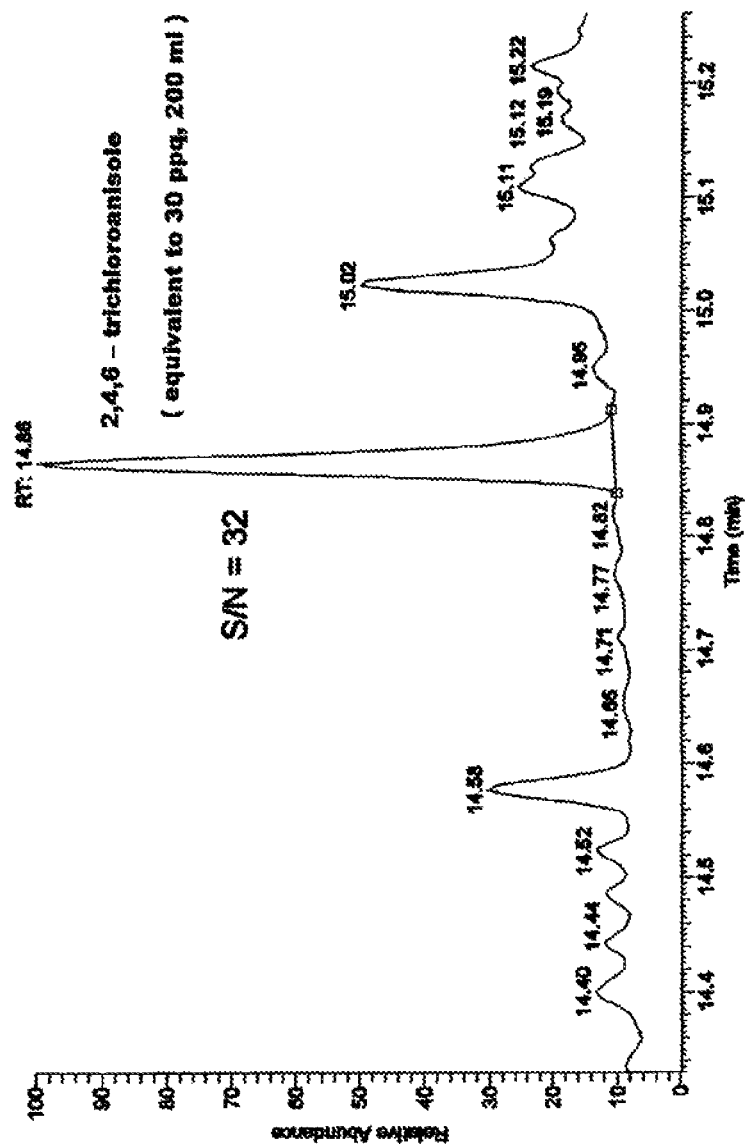
FIG. 10 is a chromatogram showing an analysis result of 2,4,6-trichloroanisole.

The analysis results are shown in FIG. 10. Since there exists no precedent report on the analysis of 30 ppq of TCA, the present example proves the high extraction efficiency of the present invention.

<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)
4) Sample flow channel temperature: 60° C.
5) Extraction time: 20 min
6) Spiral pipe made of Pyrex (registered trademark) glass
   Shape: Inner diameter of 4 mm and length of 1,200 mm;
   Installation angle: 30 degrees
7) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220 (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 min)-20° C./min-250° C. (5 min)
6) Capillary column: InertCap 5 MS/Sil, 0.25 mm I. D.×30 m, df=0.25 μm
7) Ion source: EI, 70 eV
8) SIM mode: TCA: m/z 210, 212

Example 6

On Nov. 30, 2009, 1,4-dioxane was added to the environmental criteria for the protection of human health related to water pollution of public waters and the environmental criteria related to water pollution of groundwater. The environmental criterion is 0.05 mg/L or less and the environmental criterion for groundwater is 0.05 mg/L or less. Since the environmental criterion and the groundwater criterion were added, the discharge water criterion is currently under deliberation in the expert committee for drainage regulations etc. in the central council subcommittee on water environment. A discharge water criterion proposal of 0.5 mg/L or less is under consideration. In the revised water supply law enforced since April, 2004 (Notification No. 261 by the Ministry of Health, Labor and Welfare, Jul. 22, 2003), the criterion value of 1,4-dioxane in tap water is also 0.05 mg/L. In the water supply law, the detection lower limit is required to be ¹/₁₀ or less of the criterion value.

In the water supply law, the analysis method of 1,4-dioxane includes a solid-phase extraction/solvent extraction-GC/MS method. The application of the gas-liquid contact extraction method of the present invention to 1,4-dioxane with a concentration of 5 μg/L (5 ppb), i.e. ¹/₁₀ of 0.05 mg/L, was examined. In the measurement conditions, MS measurement was performed in the SIM mode, and the monitor ion was set to m/z 58, 64. Other conditions were the same as the analysis conditions described in Example 1.

Figure 11:
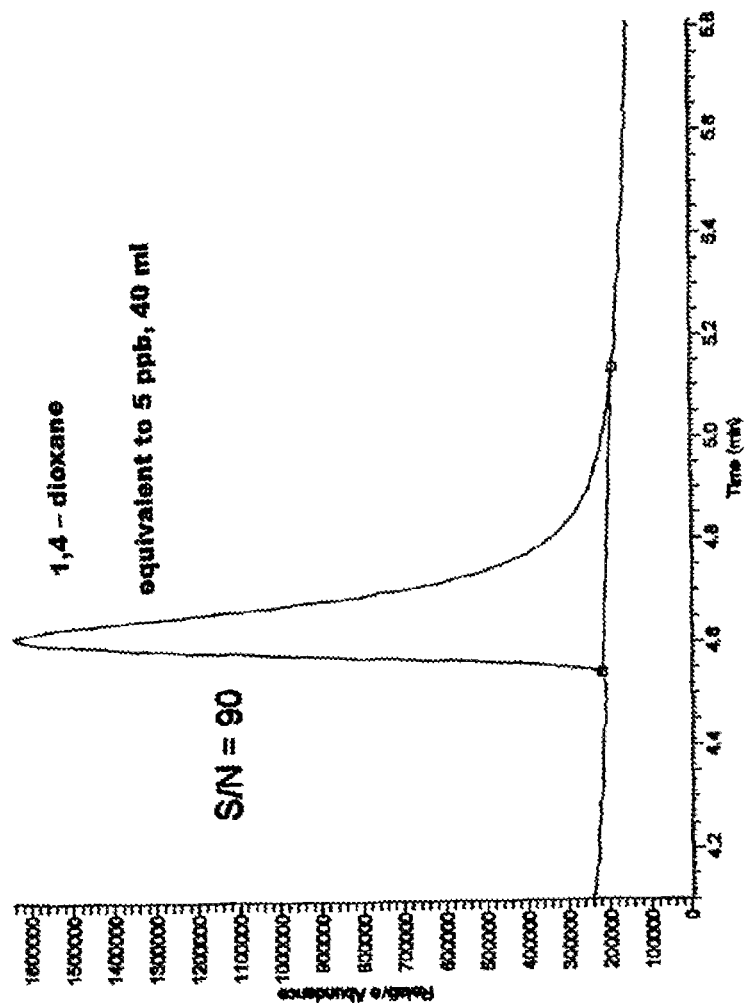
FIG. 11 is a chromatogram showing an analysis result of 1,4-dioxane in tap water.

The results are shown in FIG. 11. The tailing of the peak occurs due to the column liquid phase of the capillary column for use having micropolarity and a film thickness of 0.25 μm. In a GC analysis of 1,4-dioxane, generally a column liquid phase of the capillary column has medium polarity and a film thickness of about 2 μm. Although the optimization of column is required, the results showed that 1,4-dioxane can be analyzed by the gas-liquid contact extraction method of the present invention.

<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)
4) Sample flow channel temperature: 60° C.
5) Extraction time: 20 min
6) Spiral pipe made of Pyrex (registered trademark) glass
   Shape: Inner diameter of 4 mm and length of 1,200 mm;
   Installation angle: 30 degrees
7) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220° C. (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C. (12 min)-20° C./min-250° C. (5 min)
6) Capillary column: InertCap 5 MS/Sil, 0.25 mm I. D.×30 m, df=0.25 μm
7) Ion source: EI, 70 eV
8) SIM mode: 1,4 Dioxan: m/z 58, 64

Example 7

Analysis of Volatile Organic Compounds in Sesame Oil

Sesame oil is produced by a process of roasting at high temperature and subsequent squeezing. On this occasion, sugar and protein in the components form a pyrazine compound as flavor component by Maillard reaction. There exist many research reports on pyrazines, proposing the possibility of having bioactivity.

Figure 12:
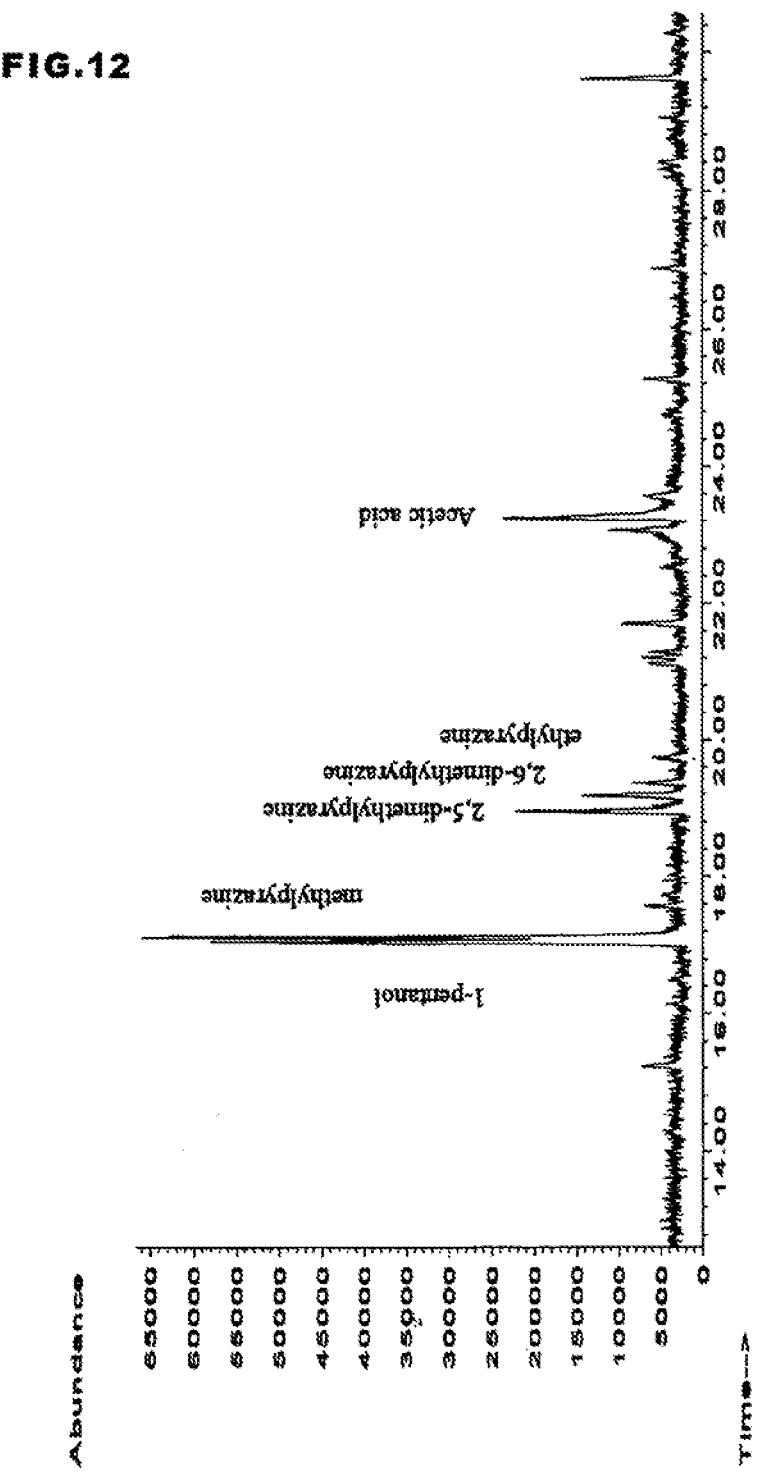
FIG. 12 is a chromatogram showing an analysis result of sesame oil.

An analysis example of the volatile organic compounds in sesame oil by the gas-liquid contact extraction method of the present invention is shown in FIG. 12. As a result of the analysis, nitrogen-containing compounds including methylpyrazole, dimethylpyrazole, and ethylpyrazole were detected.

<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)

4) Sample flow channel temperature: 60° C.
5) Extraction time: 20 min
6) Spiral pipe made of Pyrex (registered trademark) glass
   Shape: Inner diameter of 4 mm and length of 1,200 mm;
   Installation angle: 30 degrees
7) Inner surface treatment of spiral pipe:
   After the hydroxy groups on the glass surface were activated, the spiral pipe was charged with a solution of toluene in which octadecyldimethylchlorosilane had been dissolved. After a reflux for a predetermined time, the pipe was washed with toluene and dried. The chemical modification of octadecyl groups on the glass surface was thus performed and the hydrophobicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220 (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 min)
3) Analytical column flow rate: 1 ml/min
4) Split flow rate: 10 ml/min
5) GC oven temperature: 40° C., (12 min)-20° C./min-250° C. (5 min)
6) Capillary column: InertCap Pure-WAX, 0.25 mm I. D.×30 m, df=0.25 µm
7) Ion source: EI, 70 eV
8) Scan mode: m/z 10-450

Example 3

Figure 13:
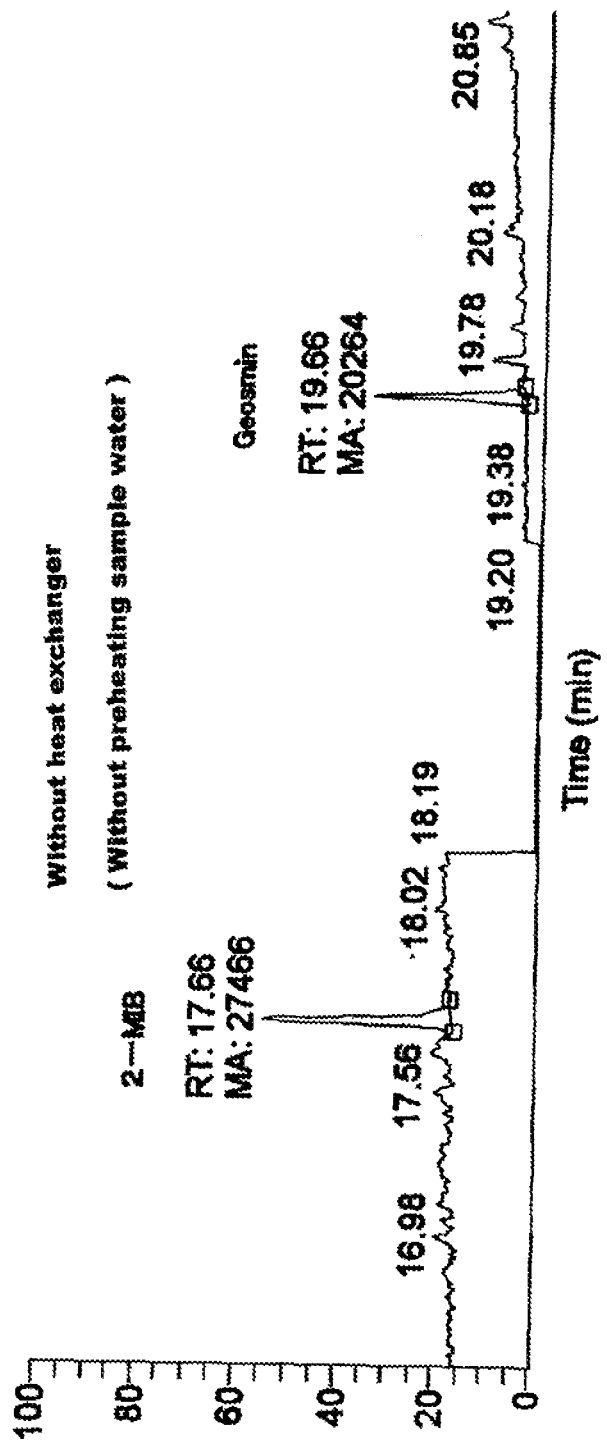
FIG. 13 is a chromatogram in a test without preheating 2-MIB and Geosimin.
Figure 14:
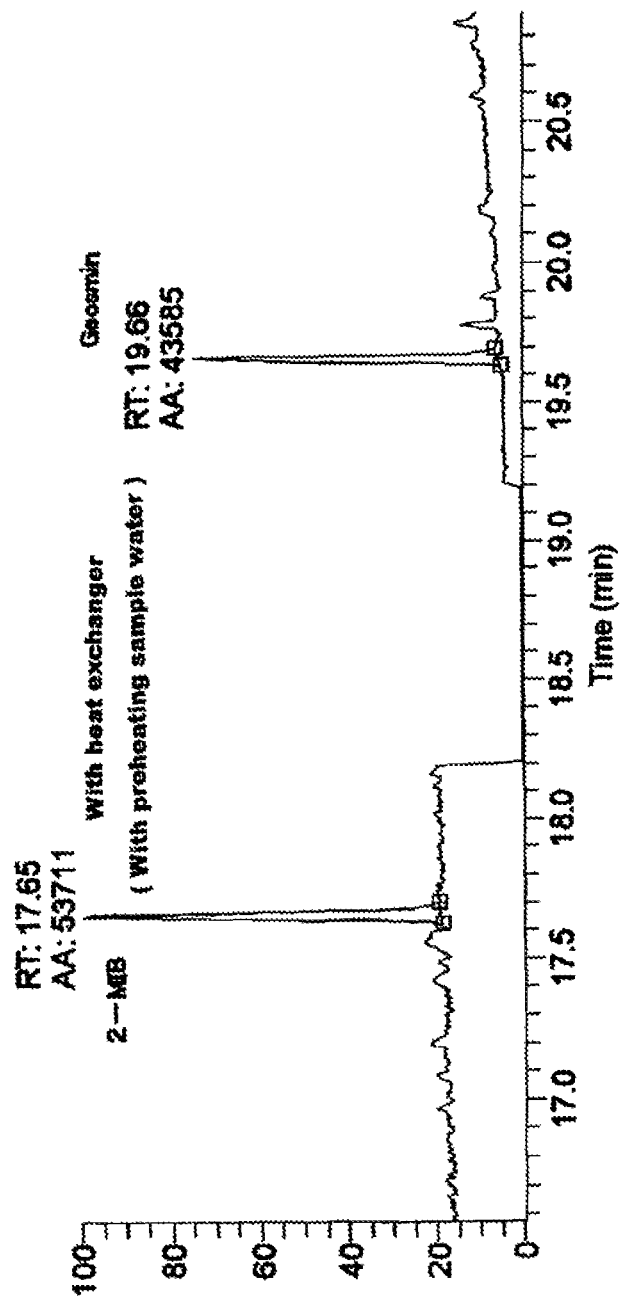
FIG. 14 is a chromatogram in the same test as above with preheating.

In the gas-liquid contact extraction method of the present invention using the automatic liquid sample supply apparatus of the present invention, the analysis "with use of a preheat pipe" and analysis "without use of a preheat pipe" were compared. The analysis results are shown in FIG. 13 and FIG. 14. It is proved that without use of a preheat pipe, the partition coefficient of analyte increased, so that the amount of mass transfer to the gas phase was reduced.
<Experimental Conditions>
(1) Extraction conditions for sample water
1) Extraction temperature of sample water: 60° C.
2) Sample water flow rate: 2 ml/min
3) Purge gas flow rate: 80 ml/min (120 kPa)
4) Sample flow channel temperature: 60° C.
5) Extraction time: 20 min
6) Spiral pipe made of Pyrex (registered trademark) glass
   Shape: Inner diameter of 4 mm and length of 1,200 mm;
   Installation angle: 30 degrees
7) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 200 mg of Tenax TA (collection tube: 3.2 mm I.D.×200 mm)
2) Temperature during collection: 60° C.
3) Collection tube heating temperature: 220 (10 minutes)
4) Desorption flow rate during heating: 11 ml/min
5) Valve temperature: 150° C.
6) Transfer line temperature: 150° C.
(3) Conditions for GCMS measurement
1) Collection tube temperature during sampling: 60° C.
2) Collection tube heating temperature during sample introduction: 220° C. (5° C./sec), (retention time: 10 mm)
3) Analytical column flow rate: 1 ml/min
4) Split flow rate: 10 ml/min
5) GC over temperature: 40° C. (12 min)-20° C./min 250° C. (5 min)
6) Capillary column: InertCap 5 MS/Sil, 0.25 mm I. D.×30 m, df=0.25 µm
7) Ion source: EI, 70 eV
3) SIM mode: 2-MIB: m/z 95, 107; Geosimin: m/z 112, 125

Example 9

In the conventional P & T method, river water cannot be analyzed due to clogging of the frit with suspended substance. The gas-liquid contact extraction method of the present invention allows river water to be analyzed. As a result, online continuous monitoring of the musty odor of river water at fixed time intervals can be conducted.

River water with increased turbidity was sampled during rainy weather. The measurement of musty odor (2-methyl-isoborneol and Geosmin) of the sampled water was performed by the gas-liquid contact extraction method of the present invention.

Figure 15:
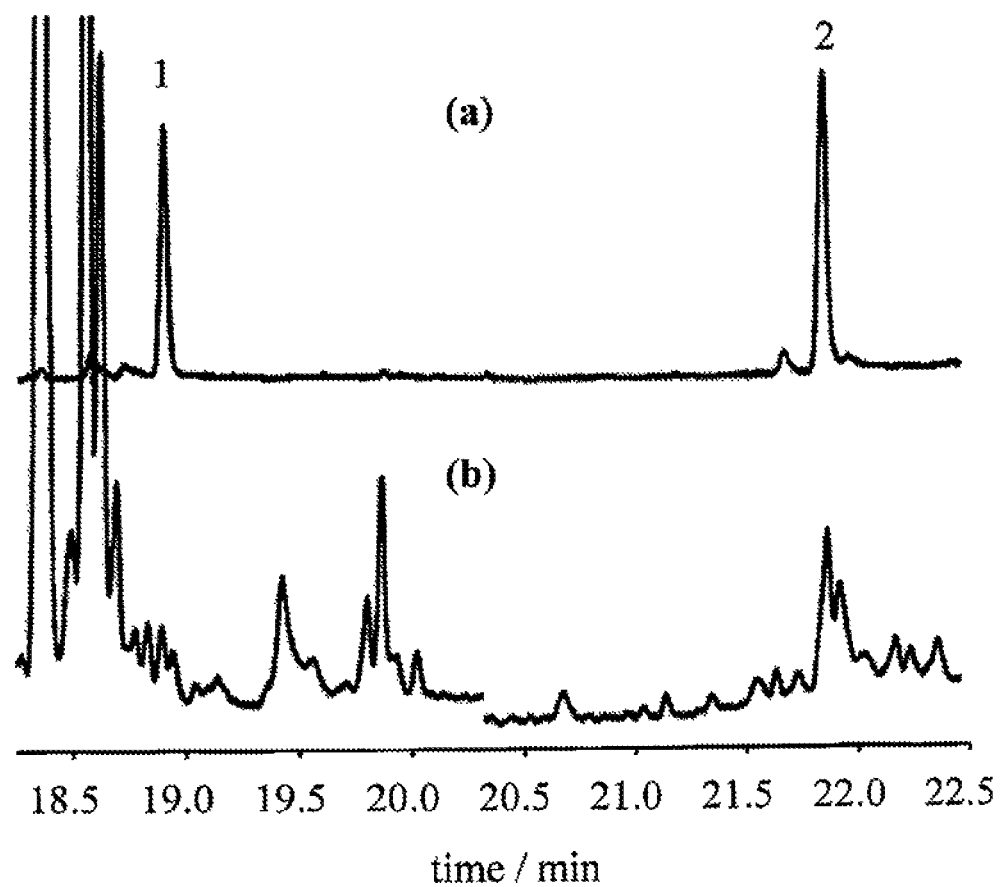
FIG. 15 is SIM chromatograms for comparing reference water (a) for musty odor with a concentration of 10 ppt and river water (b) with a turbidity of 150 degrees (kaolin).

In FIG. 15, SIM chromatograms (18.3-20.3 min: m/z 95, 20.3-22.5 min: m/z 112) are shown for comparison of reference water for musty odor with a concentration of 10 ppt (a) and river water with a turbidity of 150 degrees (kaolin) (b). The SIM chromatogram of (a) has the peak 1 of 2-MIB and the peak 2 of Geosmin. The SIM chromatogram of (b) is influenced by impurities. Many impurities were identified in the vicinity of the peaks of 2-MIB and Geosmin, and the baseline was significantly increased. It is proved that the analysis of river water can be sufficiently made.
<Experimental Conditions>
(1) Extraction conditions for river water with high turbidity
1) Extraction temperature: 60° C.
2) Flow rate: 2 mL/min
3) Purge gas flow rate: 80 mL/min
4) Extraction time: 2.5 min
5) Spiral pipe made of Pyrex (registered trademark) glass
   Shape: Inner diameter of 4 mm and length of 1,200 mm;
   Installation angle: 30 degrees
6) Inner surface treatment of spiral pipe:
   A spiral pipe was charged with 18% HCl, then washed and dried. The glass surface was thus decontaminated and the silanol groups on the glass surface were activated. Consequently, the hydrophilicity of the glass surface was improved
(2) Conditions for sample condensation
1) Collecting agent: 50 mg of Tenax TA (collection tube: 3.2 mm I.D.×300 mm)
2) Collection tube temperature during sampling: 60° C.
2) Collection tube heating temperature: 220° C. (5° C./sec, 10 minutes)
3) Desorption flow rate during heating: 2.4 mL/min
4) Valve temperature: 150° C.
5) Transfer line temperature: 150° C.
(3) Conditions for GCMS measurement
1) Analytical column flow rate: 2.4 mL/min
2) Split flow rate: 0 mL/min (splitless)
3) GC oven temperature: 40° C. (12 min)-20° C./min-250° C. (5 min)
4) Capillary column: InertCap 5 MS/Sil, 0.25 mm I. D.×30 m, df=1.0 µm
5) Ion source: EI, 70 eV
6) SIM mode: 2-MIB: m/z 95, 107; Geosimin: m/z 112, 125

Example 10

Tea includes a large amount of substance called saponin which results in high foamability. The analysis of tea cannot be performed by the conventional P & T method, since bubbles are blown up together with the purge gas so as to enter a collection tube.

Figure 16:
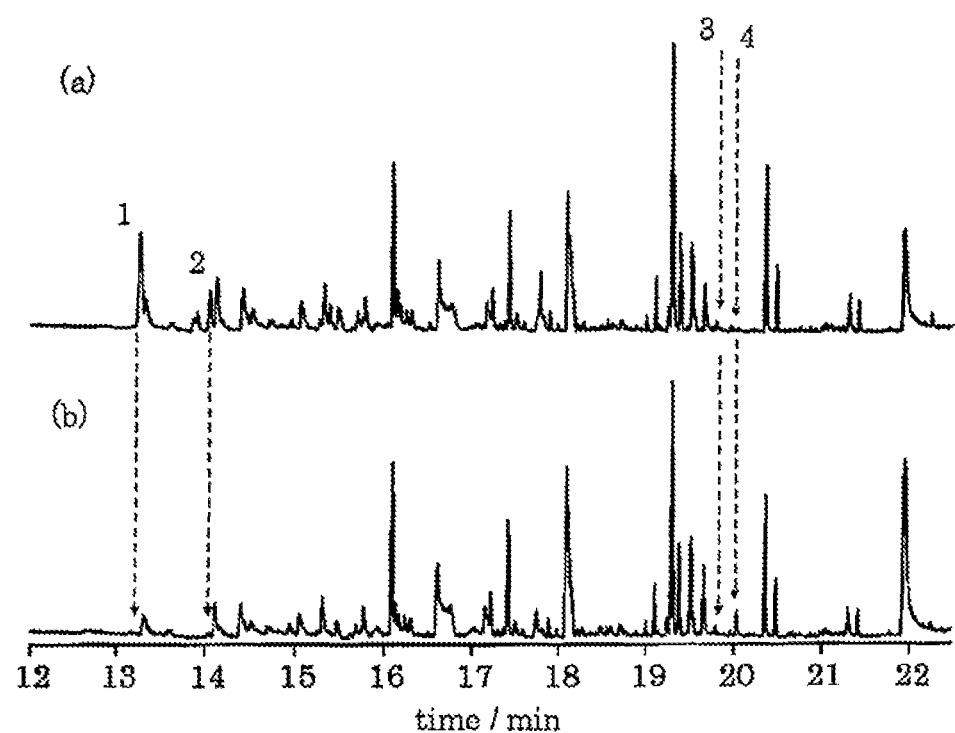
FIG. 16 is total ion current chromatograms for comparing aroma components in a commercially available tea beverage sampled immediately after unsealing and 10 days after unsealing.

The analysis of tea can be made by the gas-liquid contact extraction method of the present invention. Total ion current chromatograms (hereinafter referred to as TICC) for comparing aroma components in a commercially available tea beverage sampled immediately after unsealing and 10 days after unsealing are shown in FIG. 16.

Off-flavor components 1-octen-3-ol of the peak 1 and 2-heptenal, (E)—of the peak 2 were significantly identified in the sample (a) sampled 10 days after unsealing, which were not detected in the sample (b) sampled immediately after unsealing. In contrast, it was proved that a flavor component 1,6,10-dodecatrien-3-ol,3,7,11-trimethyl- (also known as nerolidol) of the peak 4 detected immediately after unsealing was not detected after 10 days. (5E)-3,4-dimethyl 5-pentylidenefuran-2-one (also known as bovolide) of the peak 3 was identified in both. It was proved that the analysis of tea can be made by the gas-liquid contact extraction method of the present invention.

<Experimental Conditions>
(1) Extraction conditions for commercially available tea beverage
1) Extraction temperature: 40° C.
2) Flow rate: 2 mL/min
3) Purge gas flow rate: 60 mL/min
4) Extraction time: 10 min
5) Spiral pipe made of Pyrex (registered trademark) glass
 Shape: Inner diameter of 4 mm and length of 1,200 mm;
 Installation angle: 30 degrees
6) Inner surface treatment of spiral pipe:
 A spiral pipe was charged with 18% HCl, then washed and dried. The glass surface was thus decontaminated and the silanol groups on the glass surface were activated. Consequently, the hydrophilicity of the glass surface was improved.
(2) Conditions for Sample Condensation
1) Collecting agent: 100 mg of Tenax TA (collection tube: 3.2 mm I.D.×300 mm)
2) Collection tube temperature during sampling: 40° C.
3) Collection tube heating temperature: 220° C. (5° C./sec, 10 minutes)
4) Valve temperature: 150° C.
5) Transfer line temperature: 150° C.
(3) Conditions for GCMS measurement
1) Analytical column flow rate: 1 mL/min
2) Split flow rate: 5 mL/min
3) GC oven temperature: 40° C. (12 min)-20° C./min-250° C. (5 min)
4) Capillary column: InertCap 5 MS/Sil, 0.25 mm I. D.×30 m, df=1.0 μm
5) Ion source: EI, 70 eV
6) Scan mode: m/z 15-450

Example 11

Milk has high foamability due to casein protein and whey protein. The analysis of milk cannot be performed by the conventional PT method, since bubbles are blown up together with the purge gas so as to enter a collection tube.

Figure 17:
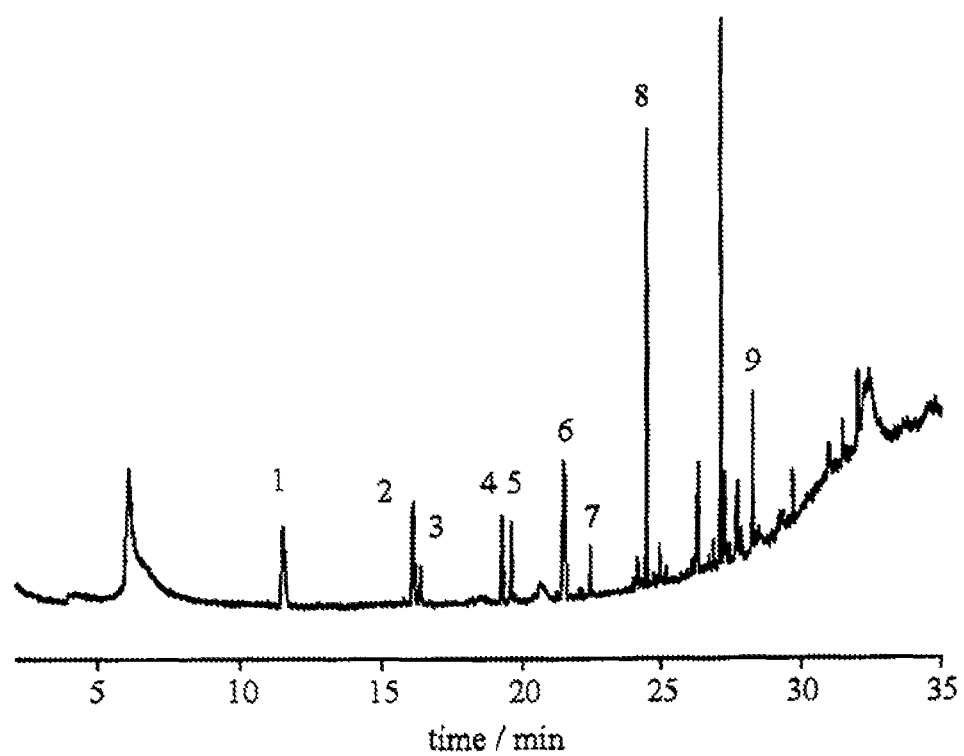
FIG. 17 is a total ion current chromatogram for analyzing volatile organic compounds in a commercially available milk.

The analysis of milk can be made by the gas-liquid contact extraction method of the present invention. The volatile organic compounds in commercially available milk were analyzed according to the present invention. The TICC is shown in the chromatogram in FIG. 17.

Acetone, 2-butanone, ethyl acetate, 4-methyl-2-pentanone, pentanal, DMDS, hexanal, heptane-2-one, nonane-2-one, and the like were identified by library search. It was proved that milk can be analyzed by the gas-liquid contact extraction method of the present invention.

<Experimental Conditions>
(1) Extraction conditions for commercially available milk
1) Extraction temperature: 40° C.
2) Flow rate: 2 mL/min
3) Purge gas flow rate: 60 mL/min
4) Extraction time: 10 min
5) Spiral pipe made of Pyrex (registered trademark) glass
 Shape: Inner diameter of 4 mm and length of 1,200 mm;
 Installation angle: 30 degrees
6) Inner surface treatment of spiral pipe:
 A spiral pipe was charged with 18% HCl, then washed and dried. The glass surface was thus decontaminated and the silanol groups on the glass surface were activated. Consequently, the hydrophilicity of the glass surface was improved.
(2) Conditions for sample condensation
1) Collecting agent: 100 mg of Tenax TA (collection tube: 3.2 mm I.D.×300 mm)
2) Collection tube temperature during sampling: 40° C.
3) Collection tube heating temperature: 220° C. (5° C./sec, 10 minutes)
4) Valve temperature: 150° C.
5) Transfer line temperature: 150° C.
(3) Conditions for GCMS measurement
1) Analytical column flow rate: 1 mL/min
2) Split flow rate: 5 mL/min
3) GC oven temperature: 40° C. (12 min)-20° C./min-250° C. (5 min)
4) Capillary column: InertCap AQUATIC-2, 0.25 mm I. D.×40 m, df=1.4 μm
5) Ion source: EI, 70 eV
6) Scan mode: m/z 15-450

INDUSTRIAL APPLICABILITY

The present invention allows for easy analysis of an analyte having a large partition coefficient, an analyte having high water solubility, or an analyte having a low olfactory threshold, which has been conventionally difficult. Furthermore, in quality control of tap water, river water, or beverage, unmanned sample introduction including sampling, extraction, and analysis can be continuously performed without manual operation for a long time.

We claim:

1. A gas-liquid contact extraction method using a gas-liquid contact extractor to which a sample liquid is continuously introduced from above and a purge gas from beneath, for extracting an analyte in the sample liquid by gas-liquid contact between the sample liquid and the purge gas, the method comprising discharging the sample liquid through a liquid sump provided to a discharge pipe connected to a bottom of the gas-liquid contact extractor, while blocking outflow of the purge gas from the liquid sump, wherein the sample liquid is preheated to an extraction temperature in the gas-liquid contact extractor prior to supplying the sample liquid to the gas-liquid contact extractor.

2. The gas-liquid contact extraction method according to claim 1, wherein a water-soluble component having a partition coefficient K larger than 1 or an analyte having an olfactory threshold lower than 10 ppt (pg/ml) existing in the sample liquid is gas-liquid contact extracted.

3. The gas-liquid contact extraction method according to claim 2, wherein the gas-liquid contact extractor is provided in a temperature-controlled oven, and a temperature of a flow channel to a collection tube for condensing the gas-liquid contact extracted analyte is set to a temperature equal to or higher than an oven temperature (gas-liquid extraction temperature), so that the gas-liquid extracted analyte is condensed in the collection tube.

4. The gas-liquid contact extraction method according to claim 1, wherein the gas-liquid contact extractor is provided in a temperature-controlled oven, and a temperature of a flow channel to a collection tube for condensing the gas-liquid contact extracted analyte is set to a temperature equal to or higher than an oven temperature (gas-liquid extraction temperature), so that the gas-liquid extracted analyte is condensed in the collection tube.

5. A gas-liquid contact extraction apparatus comprising a gas-liquid contact extractor to be supplied with a liquid sample from above and a purge gas from beneath, a discharge pipe connected to the bottom of the gas-liquid contact extractor, a liquid sump provided to the discharge pipe for discharging the sample liquid and blocking the discharge of the purge gas, and a collection tube for condensing the gas-liquid contact extracted analyte, wherein the gas-liquid contact extractor is provided in a temperature-controlled oven and is adapted to provide a temperature of a flow channel to the collection tube for condensing the gas-liquid contact extracted analyte set to a temperature equal to or higher than an oven temperature.

6. The gas-liquid contact extraction apparatus according to claim 5, wherein the contact surface of the gas-liquid contact extractor with a sample liquid is surface treated to achieve a spread wetting state.

7. An automatic liquid sample supply apparatus comprising a liquid sample supply part connected to the gas-liquid contact extraction apparatus according to claim 6 through a syringe pump and a selector valve for switching a flow channel, allowing an analyte gas-liquid contact extracted by the gas-liquid contact extraction apparatus to be sent to a collection tube.

8. The gas-liquid contact extraction apparatus according to claim 6, wherein the surface treatment is any one of a hydrophilic treatment and a water repellent treatment.

9. An automatic liquid sample supply apparatus comprising a liquid sample supply part connected to the gas-liquid contact extraction apparatus according to claim 8 through a syringe pump and a selector valve for switching a flow channel, allowing an analyte gas-liquid contact extracted by the gas-liquid contact extraction apparatus to be sent to a collection tube.

10. An automatic liquid sample supply apparatus comprising a liquid sample supply part connected to the gas-liquid contact extraction apparatus according to claim 5 through a syringe pump and a selector valve for switching a flow channel, allowing an analyte gas-liquid contact extracted by the gas-liquid contact extraction apparatus to be sent to a collection tube.

11. A gas-liquid contact extraction method using a gas-liquid contact extractor to which a sample liquid is continuously introduced from above and a purge gas from beneath, for extracting an analyte in the sample liquid by gas-liquid contact between the sample liquid and the purge gas, the method comprising discharging the sample liquid through a liquid sump provided to a discharge pipe connected to a bottom of the gas-liquid contact extractor, while blocking outflow of the purge gas from the liquid sump, wherein the gas-liquid contact extractor is provided in a temperature-controlled oven, and a temperature of a flow channel to a collection tube for condensing the gas-liquid contact extracted analyte is set to a temperature equal to or higher than an oven temperature (gas-liquid extraction temperature), so that the gas-liquid extracted analyte is condensed in the collection tube.

12. The gas-liquid contact extraction method according to claim 11, wherein a water-soluble component having a partition coefficient K larger than 1 or an analyte having an olfactory threshold lower than 10 ppt (pg/ml) existing in the sample liquid is gas-liquid contact extracted.

* * * * *